United States Patent
Gunnes et al.

(10) Patent No.: US 10,640,536 B2
(45) Date of Patent: May 5, 2020

(54) POLYMYXINS, COMPOSITIONS, METHODS OF MAKING AND METHODS OF USE

(71) Applicant: XELLIA PHARMACEUTICALS APS, Copenhagen (DK)

(72) Inventors: Solvi Gunnes, Lommedalen (NO); Vidar Bjornstad, Oslo (NO); Torben Koch, Copenhagen Nv (DK); Claes Melander, Malmo (SE); Martin Mansson, Oslo (NO)

(73) Assignee: XELLIA PHARMACEUTICALS APS, Copenhagen S (DK)

( * ) Notice: Subject to any disclaimer, the term of this patent is extended or adjusted under 35 U.S.C. 154(b) by 0 days.

(21) Appl. No.: 14/760,222

(22) PCT Filed: Jan. 9, 2014

(86) PCT No.: PCT/EP2014/050320
§ 371 (c)(1),
(2) Date: Jul. 10, 2015

(87) PCT Pub. No.: WO2014/108469
PCT Pub. Date: Jul. 17, 2014

(65) Prior Publication Data
US 2016/0002296 A1 Jan. 7, 2016

Related U.S. Application Data

(60) Provisional application No. 61/904,793, filed on Nov. 15, 2013, provisional application No. 61/751,341, filed on Jan. 11, 2013.

(51) Int. Cl.
*A61K 38/00* (2006.01)
*C07K 7/62* (2006.01)
(52) U.S. Cl.
CPC ............... *C07K 7/62* (2013.01); *A61K 38/00* (2013.01); *Y02A 50/473* (2018.01)
(58) Field of Classification Search
None
See application file for complete search history.

(56) References Cited

U.S. PATENT DOCUMENTS 3,317,506 A 5/1967 Wilkinson
5,767,068 A 6/1998 Vandevanter et al.
(Continued)

FOREIGN PATENT DOCUMENTS

DE 1906699 A1 2/1970
FR 1586834 A 3/1970
(Continued)

OTHER PUBLICATIONS

Shorin et al ("Antibacterial Activity, Toxicity and Medicinal Properties of Monomycin and Colimycin Methanesulfonates" Database CA [on-line]Chemical Abstracts Service, Columbus, Ohio, Database accession No. 56:38870; 4 pages (1961)).*
Bergen et al (Antimicrob Agents Chemother. Jun. 2006; 50(6): 1953-1958).*
Suter et al. (The sulfomethylation reaction, Jun. 16, 1945) (Year: 1945).*
CN102531955A machine translation (Year: 2011).*
International Search Report and Written Opinion; International Application No. PCT/EP2014/050320; International Filing Date Jan. 9, 2014; dated May 22, 2014; 9 pages.
Storm et al.; "Polymyxin and Related Peptide Antibiotics"; Annual Review of Biochemistry; 46; pp. 723-763; (1977).
Govaerts et al.; "Mass Spectrometric Fragmentation of Cyclic Peptides Belonging to the Polymyxin and Colistin Antibiotics Studied by Ion Trap and Quadrupole/Orthogonal-Acceleration Time-of-Flight Technology"; Rapid Comm. in Mass Spectrometry; 16; pp. 823-833; (2002).
Magee et al.; "Discovery of Dap-3 Polymyxin Analogues for the Treatment of Multidrug-Resistant Gram-Negative Nosocomial Infections"; Journal of Medicinal Chemistry; 53(12); pp. 5079-5093; (2013).

(Continued)

*Primary Examiner* — Sergio Coffa
(74) *Attorney, Agent, or Firm* — Cantor Colburn LLP

(57) ABSTRACT

Disclosed herein is a composition comprising at least one polymyxin or a salt thereof represented by formula (I) wherein $R^1$ is an aliphatic linear or branched $C_6$-$C_{10}$ acyl group, or (I') $R^5$ is —$CH(CH_3)_2$, —$CH_2CH(CH_3)_2$, —$CH(CH_3)CH_2CH_3$, or —$CH_2C_6H_5$; $R^6$ is —$CH(CH_3)_2$, —$CH_2CH(CH_3)_2$, or —$CH(CH_3)CH_2CH_3$; each of $R^2$, $R^3$, $R^4$, $R^7$ and $R^8$ is either —$(CH_2)_xCH_2NH_2$ or —$(CH_2)_xCH_2N(CH_2SO_3M)_2$; wherein x is 0 or 1; wherein M is a monovalent cation; and wherein at least three of $R^2$, $R^3$, $R^4$, $R^7$ and $R^8$ are —$(CH_2)_xCH_2N(CH_2SO_3M)_2$.

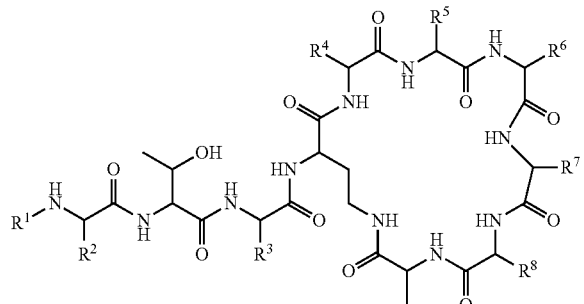

(I)

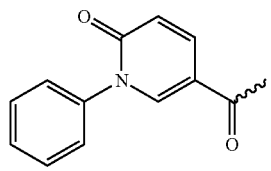

(I')

21 Claims, 15 Drawing Sheets

(56) References Cited

U.S. PATENT DOCUMENTS

| | | | | |
|---|---|---|---|---|
| 8,193,354 | B2* | 6/2012 | Ujagare | C07H 19/073 536/28.5 |
| 2003/0143162 | A1 | 7/2003 | Speirs et al. | |
| 2004/0022740 | A1 | 2/2004 | Baker et al. | |
| 2008/0066739 | A1 | 3/2008 | Lemahieu et al. | |
| 2012/0316105 | A1 | 12/2012 | Magee et al. | |
| 2017/0218024 | A1 | 8/2017 | Bjornstad | |
| 2017/0239321 | A1 | 8/2017 | Bencic | |

FOREIGN PATENT DOCUMENTS

| | | |
|---|---|---|
| WO | 19890009626 A1 | 10/1989 |
| WO | 199820836 | 5/1998 |
| WO | 2008025560 A1 | 3/2008 |
| WO | 2012168820 A1 | 12/2012 |
| WO | 2014108469 A1 | 7/2014 |
| WO | 2014195405 A1 | 12/2014 |

OTHER PUBLICATIONS

Van den Bossche et al.; "Identification of Impurities in Polymyxin B and Colistin Bulk Sample Using LiquidChromatography Coupled to Mass Spectrometry"; Talanta; 83; pp. 1521-1529; (2011).

Wishart et al.; "1H, 13C and 15N Chemical Shift Referencing in Biomolecular NMR"; Journal of Biomolecular NMR; 6; pp. 135-140; (1995).

He et al.; "Pharmacokinetics of Four Different Brands of Colistimethate and Formed Colistin in Rats"; J Antimicrob Chemother; 68; pp. 2311-2317; (2013).

Bossche et al.; "Identification of impurities in Polymyxin B and Colistin Bulk Sample Using Liquid Chromatography Coupled to Mass Spectrometry"; Talanta; 82; pp. 1521-1529; (2011).

European Medicines Agency Assessment report of polymixin-based products, EMA/CHMP/153652/2015, dated Feb. 26, 2015.

European Medicines Agency: "Review Under Article 5(3) of Regulation EC(No) 726-2004; Polymyxin-based products"; retrieved from the Internet: URL:http://www.ema.eurooa.eu/docs/en_GB/document_library/Report/2015105/WC500187326.pdf. Retrieved on Sep. 7, 2015.

Healan et al.; "Stability of Colistirnethate Sodium in Aqueous Solution"; AAC.ASM.Org; 56(12); pp. 6432-6433; (2012); downloaded Mar. 23, 2017 http://aac.asm.org.

Kamin et al.; "Inhalation Solutions—which one are allowed to be mixed? Physico-chemical Coomoatibility of Drug Solutions in Nebulizers"; Journal of Cystic Fibrosis; 5; pp. 205-213; (2006).

Li et al.; "Evaluation of Colistin as an Agent Against Multi-resistant Gram-negative Bacteria"; International Journal of Antimicrobial Agents; 25(1); pp. 11-25; (2005).

Li et al.; "Stability of Colistin and Colistin Methanesulfonate in Aqueous Media and Plasma as Determined by High-Performance Liquid Chromatography"; Antimicrobial Agents and Chemotherapy; 47(4); pp. 1364-1370; (2003).

Li et al; "Defining the Dosage Units for Colistin Methanesulfonate: Urgent Need for International Harmonization"; Antimicrobial Agents and Chemotherapy; 50(12); pp. 4231-4232; (2006).

McMillian et al.; "Sodium Colistimethate I: Dissociations of Aminomethanesulfonates in Aqueous Solution"; Journal of Pharmaceutical Sciences; ; 58(6); pp. 730-737; (1969).

Wallace et al.; "Self-assembly Behaviour of Colistin and its Prodrug Colistin Methanesulfonate: Implications for Solution Stability and Solubilization"; J. Phys Chem B., Author Manuscript: 114(14); pp. 4836-4840; (2010).

Wallace et al.; "Stability of Colistin Methanesulfonate in Pharmaceutical Products and Solutions for Administration to Patients"; Antimicrobial Agents and Chemotherapy; pp. 3047-3051; (2008).

Young et al.; "Optimization of Anti-Pseudornonal Antibiotics for Cystic Fibrosis Pulmonary Exacerbations: IV. Colistimethate Sodium"; Pediatric Pulmonology; 48; pp. 1-7; (2013).

Athanassa et al.; "Pharmacokinetics of Inhaled Colistimethate Sodium (CMS) in Mechanically Ventilated Critically Ill Patients"; Intensive Care Med 38; pp. 1779-1786; (2012).

Barnett et al.; "Sodium Sulphomethyl Derivatives of Polymyxins"; Birt. J. Pharmacol, 23, pp. 552-574; (1964).

BioPharm International Editors; "Biopharmaceutical Manufacturing Using Blow-Fill-Seal Technology"; in BioPharm International; 24(7); 7 pages; (2011).

Keller et al.; "Performance Characteristics of Colistimethate Sodium Solutions (Colistin) Delivered by Jet Nebulizers Compared to the eFlow SCF Electronic Nebulizer"; North American Cystic Fibrosis Conference, St. Louis, USA, Oct. 14-17, 2004.

Kassamali et al.; "Polymyxins: Wisdom Does Not Always Come With Age"; Clinical Infectious Diseases; 57; pp. 877-883; (2013).

Brochet et al.; "Comparative Efficacy of Two Doses of Nebulized Colistimethate for the Eradication of Pseudomonas Aeruginosa in Children with Cystic Fibrosis"; Can Respir J; 14(8); pp. 473-479; (2007).

Falagas et al.; "Use of International Units When Dosing Colistin Will Help Decrease Confusion Related to Various Formulations of the Drug Around the World"; Antimicrobial Agents and Chemotherapy; pp. 2274-2275; (2006).

Coly-Mycin M Parenteral (Colistimethate for Injection, USP), Prescribing Information as of Feb. 2011; JHP Pharmaceuticals Ref: 300818F, 5 pages.

Yapa et al., Pulmonary and Systemic Pharmacokinetics of Inhaled and Intravenous Colistin Methanesulfonate in Cystic Fibrosis Patients: Targeting Advantage of Inhalation Administration; Antimicrobial Agents and Chemotherapy; 58(5); pp. 2570-2579; (2014).

Particles in Injections; printed Mar. 26, 2019; 4 pages; http://www.uspbpep.com/usp32/pub/data/v32270/usp32nf27s0_c1.html.

Tawde, Suprita A.; "Particulate Matter in Injectables: Main Cause for Recalls"; J. Pharmacovigil; 3(1); e128; 3 pages; (2014).

Tobramycin Inhalation Soluation; printed Mar. 22, 2019; 4 pages; http://www.uspbpep.com/usp32/pub/data/v32270/usp32nf27s)_m83766.html; 4 pages.

* cited by examiner

| Polymyxin | Y | $R_a$ | $R_b$ | $R_c$ | MW |
|---|---|---|---|---|---|
| E1 | -CH$_2$CH(CH$_3$)$_2$ | CH$_3$ | H | CH$_3$ | 2328.3 |
| E2 | -CH$_2$CH(CH$_3$)$_2$ | H | H | CH$_3$ | 2314.3 |
| E3 | -CH$_2$CH(CH$_3$)$_2$ | CH$_3$ | H | H | 2314.3 |
| E1-i | -CH(CH$_3$)CH$_2$CH$_3$ | CH$_3$ | H | CH$_3$ | 2328.3 |
| E1-7MOA | -CH$_2$CH(CH$_3$)$_2$ | CH$_3$ | CH$_3$ | H | 2328.3 |

POLYMYXINS, COMPOSITIONS, METHODS OF MAKING AND METHODS OF USE

RELATED APPLICATIONS

This application is a 371 of PCT/EP2014/050320 filed on Jan. 9, 2014, which claims priority to Priority is claimed to U.S. Provisional Application No. 61/751,341, filed on Jan. 11, 2013, and U.S. Provisional Application No. 61/904,793, filed on Nov. 15, 2013, under the provisions of 35 U.S.C. 119 and the International Convention for the protection of Industrial Property, the subject matter of said applications is incorporated by reference.

FIELD OF THE INVENTION

Disclosed herein is a composition comprising at least one polymyxin or a salt thereof represented by formula (I).

BACKGROUND

Polymyxins were discovered in 1947 as antibiotics produced by *Bacillus polymyxa*. Polymyxins are antibiotic decapeptides containing a heptapeptide ring and a N-terminal amide coupled fatty acid. Today, two commercial Polymyxin mixtures are in clinical use; Polymyxin B and Polymyxin E (Colistin). Both mixtures comprise a variety of components as described by Goevaerts et al 2002 and Van den Bossche et al 2011. According to EP pharmacopoeia, Colistin should comprise more than 77% of Polymyxin E1, E2, E3, E1-i and E1-7MOA, but less than 10% of each of the minor components Polymyxin E3, E1-i and E1-MOA.

Due to toxicity associated with Colistin, the mixture was improved by sulfomethylation in the 1950'ties. The sulfomethylated Colistin is called Colistimethate sodium (CMS) which is considered to be a prodrug of Colistin. CMS is still in clinical use as a last-line treatment option for multidrug-resistant organisms such as *Pseudomonas aeruginosa, Aqinetobacter baumannii, Klebsiella pneumonia* and other Gram negative pathogens. For many years, solutions of CMS have also been administered by nebulization into the lungs of patients with cystic fibrosis (CF) to manage colonization or infections caused by *P. aeruginosa*.

The fact that commercial CMS products contain a complex mixture of derivatives of different Polymyxins has several consequences. The foremost of these relates to the therapeutic value of any marketed product. Since CMS may be considered a Colistin-reservoir once injected or inhaled into the body, it is of importance that an appropriate amount of CMS is transformed into colistin before it is excreted. If not, the serum level of Colistin may not reach a level sufficiently high to kill or prevent growth of the pathogenic bacterium targeted. Thus, by being able to manufacture a CMS with a controlled amount of substituents, either in mixture or as mono component, increase therapeutic potential by prevention of under- or over-dosing. It may also increase the prodrug characteristics of the molecule by affecting the hydrolysis rate of the CMS (the in vivo conversion rate of CMS to colistin).

SUMMARY

A composition comprising at least one polymyxin or a salt thereof represented by formula (I)

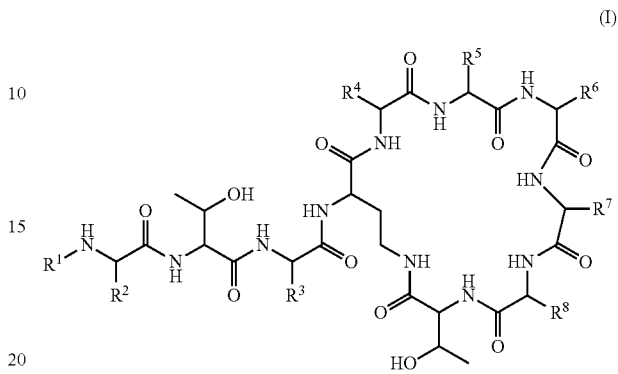

(I)

wherein
$R^1$ is an aliphatic linear or branched $C_6$-$C_{10}$ acyl group, or

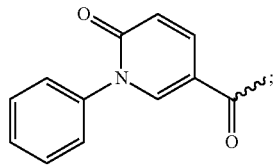

$R^5$ is $-CH(CH_3)_2$, $-CH_2CH(CH_3)_2$, $-CH(CH_3)CH_2CH_3$, or $-CH_2C_6H_5$;
$R^6$ is $-CH(CH_3)_2$, $-CH_2CH(CH_3)_2$, or $-CH(CH_3)CH_2CH_3$;
each of $R^2$, $R^3$, $R^4$, $R^7$ and $R^8$ is either $-(CH_2)_xCH_2NH_2$ or $-(CH_2)_xCH_2N(CH_2SO_3M)_2$;
wherein x is 0 or 1;
wherein M is a monovalent cation; and
wherein at least three of $R^2$, $R^3$, $R^4$, $R^7$ and $R^8$ are $-(CH_2)_xCH_2N(CH_2SO_3M)_2$.

DETAILED DESCRIPTION

DEFINITIONS

Figure 1:
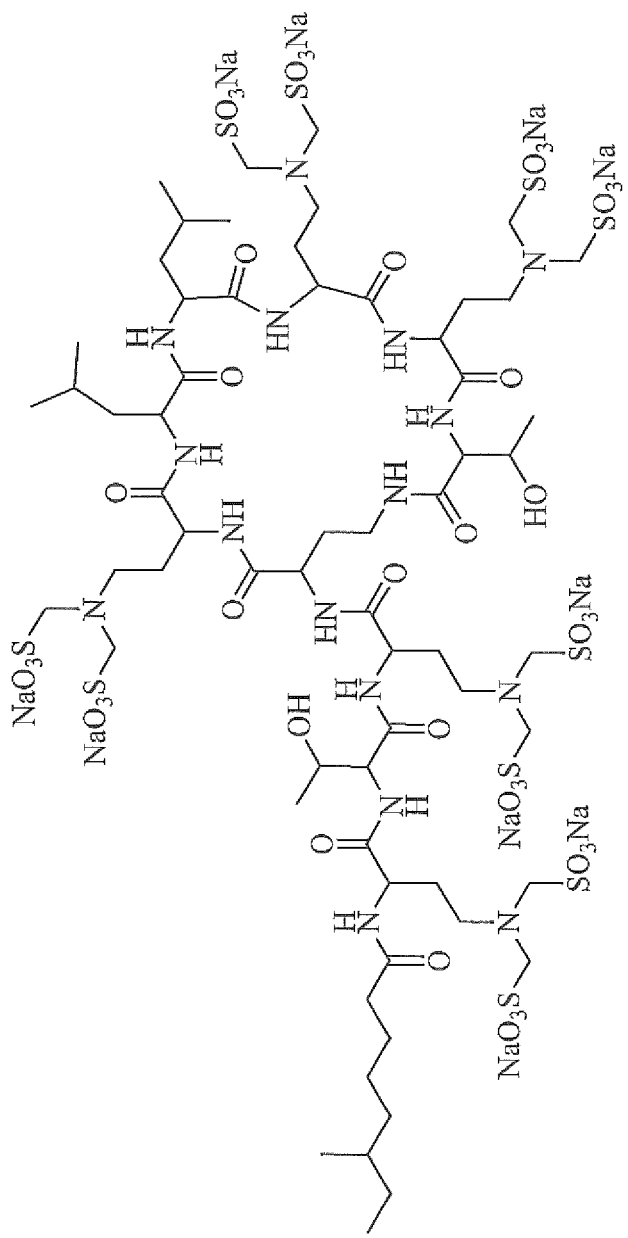
FIG. 1. Structure of PE1-$(SM)_{10}^{1,3,5,8,9}$.

The phrase "a" or "an" entity as used herein refers to one or more of that entity; for example, a compound refers to one or more compounds or at least one compound. As such, the terms "a" (or "an"), "one or more", and "at least one" can be used interchangeably herein.

The terms "optional" or "optionally" as used herein means that a subsequently described event or circumstance may but need not occur, and that the description includes instances where the event or circumstance occurs and instances in which it does not. For example, "optional bond" means that the bond may or may not be present, and that the description includes single, double, or triple bonds.

The term "stereoisomer" has its plain and ordinary meaning.

The polymyxin or salt thereof represented by formula (I) contains a number of carbon-based stereocenters that may have stereochemical designations of natural (L-) and unnatural (D-) amino acid residues. It will be understood that the moieties —CH(CH$_3$)CH$_2$CH$_3$ and —CH(OH)CH$_3$ contain carbon-based stereocenters that have the same stereochemistry as the radicals found in L-isoleucine and L-threonine.

The expression "an aliphatic linear or branched C$_6$-C$_{10}$ acyl group," as described herein, refers to a substituent containing a carbonyl moiety and a non-carbonyl moiety and includes the acyl groups found in known polymyxin compounds, which include, but are not limited to heptanoyl, methylheptanoyl (including (S)-6-methylheptanoyl), octanoyl, methyloctanoyl (including (S)-6-methyloctanoyl, (S)-7-methyloctanoyl), nonanoyl, methylnonanoyl (including (S)-6-methylnonanoyl, (S)-7-methylnonanoyl, and (S)-8-methylnonanoyl) and decanoyl.

The term "salts" or "salt thereof" as described herein, refers to a compound comprising a cation and an anion, which can prepared by any process known to one of ordinary skill, e.g., by the protonation of a proton-accepting moiety and/or deprotonation of a proton-donating moiety. Alternatively, the salt can be prepared by either a cation/anion metathesis or a cation/anion exchange reaction.

The expression "—CH$_2$CH$_2$NH$_2$" is understood to cover either —CH$_2$CH$_2$NH$_2$ or —CH$_2$CH$_2$NH$_3$$^+$ depending on the pH of the medium.

The term "M is a monovalent cation" as described herein, refers to a cationic species containing a single positive charge, examples of which include, but are not limited to Li$^+$, Na$^+$, K$^+$, H$_m$N(C$_{1-4}$alkyl)$^+$, where m is 0-4 and n is 0-4 with the proviso that m+n=4.

The term "C$_{1-4}$-alkyl" as described herein, refers to a straight or branched chain alkyl group containing 1 to 4 carbon atoms. Examples of C$_{1-4}$ alkyl groups include, but are not limited to methyl, ethyl, propyl, i-propyl, and n-butyl.

The term "DAB" as described herein, refers the radical derived from 2,4-diaminobutanoic acid, in which the carbon atom adjacent to the carbonyl carbon (i.e., the α-carbon) has a stereochemistry designated as the L-configuration. L-DAB is alternatively referred to in the literature as L-DBU.

The term "DAB residue" as described herein, refers to a 2,4-diaminobutyrate compound amide-coupled to at least one amino acid. The naturally occuring polymyxins usually comprise 6 DAB residues of which 5 have a free γ-amino group.

The term "sulfomethyl" as described herein refers to the —CH$_2$SO$_3$M moiety, where M is as defined above. The sulfonate (—SO$_3$) moiety can be in acidic form, but in a physiologic environment (in vivo) it will have a negative charge and will have an associated cation, such as M.

The term "DAP" as described herein refers to the compound 2,3 diaminopropionate.

The term "DAP residue" as described herein refers to a 2,3-diaminopropionate compound amide-coupled to at least one amino acid.

The term "FA" as described herein is an abbreviation for the expression "fatty acyl," and is covered by the expression "an aliphatic linear or branched C$_6$-C$_{10}$ acyl group," as related to the at least one polymyxin or salt thereof represented by formula (I).

The term "in an amount of at least X % by UHPLC" as described herein is to be understood as the relative integrated area of the pertaining peak(s) in the chromatogram resulting from an UHPLC method as described in the Materials and Methods-part of this application.

The term "purity of more than Y % based on UHPLC chromatogram" is to be understood as the relative integrated area of the pertaining peak(s) in the chromatogram resulting from an UHPLC method as described in the Materials and Methods-part of this application.

A first embodiment is directed to a composition comprising at least one polymyxin or a salt thereof represented by formula (I)

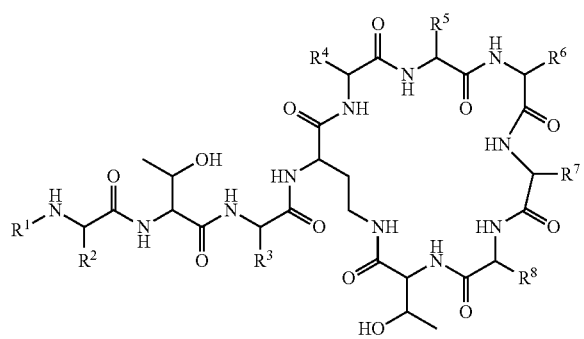

wherein

R$^1$ is an aliphatic linear or branched C$_6$-C$_{10}$ acyl group, or

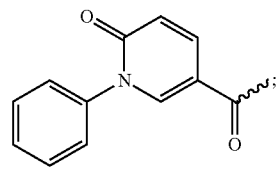

R$^5$ is —CH(CH$_3$)$_2$, —CH$_2$CH(CH$_3$)$_2$, —CH(CH$_3$)CH$_2$CH$_3$, or —CH$_2$C$_6$H$_5$;

R$^6$ is —CH(CH$_3$)$_2$, —CH$_2$CH(CH$_3$)$_2$, or —CH(CH$_3$)CH$_2$CH$_3$;

each of R$^2$, R$^3$, R$^4$, R$^7$ and R$^8$ is either —(CH$_2$)$_x$CH$_2$NH$_2$ or —(CH$_2$)$_x$CH$_2$N(CH$_2$SO$_3$M)$_2$;

wherein x is 0 or 1;
wherein M is a monovalent cation; and
wherein at least three of $R^2$, $R^3$, $R^4$, $R^7$ and $R^8$ are
—$(CH_2)_xCH_2N(CH_2SO_3M)_2$.

In a first aspect of the first embodiment, $R^1$ is heptanoyl, methylheptanoyl, octanoyl, methyloctanoyl, nonanoyl, methylnonanoyl or decyl.

In a second aspect of the first embodiment, $R^1$ is heptanoyl, (S)-6-methylheptanoyl, octanoyl, (S)-6-methyloctanoyl, (S)-7-methyloctanoyl, nonanoyl, (S)-6-methylnonanoyl, (S)-7-methylnonanoyl, (S)-8-methylnonanoyl or decanoyl.

In a third aspect of the first embodiment, the previously described compositions are characterized in that M is selected from the group consisting of $Na^+$, $K^+$, $H_m N(C_{1-4}alkyl)_n^+$, or combinations thereof, where m is 0-4 and n is 0-4 with the proviso that m+n=4.

In a fourth aspect of the first embodiment, x is 1 and M is $H^+$, $Na^+$ or $K^+$.

In a fifth aspect of the first embodiment, x is 1 and M is $H^+$, $Na^+$ or K+ and three of $R^2$, $R^3$, $R^4$, $R^7$ and $R^8$ are —$CH_2CH_2N(CH_2SO_3M)_2$.

In a sixth aspect of the first embodiment, x is 1 and M is $H^+$, $Na^+$ or $K^+$ and each of $R^2$, $R^4$ and $R^8$ is —$CH_2CH_2N(CH_2SO_3M)_2$.

In a seventh aspect of the first embodiment, x is 1 and M is $H^+$, $Na^+$ or $K^+$ and four of $R^2$, $R^3$, $R^4$, $R^7$ and $R^8$ are —$CH_2CH_2N(CH_2SO_3M)_2$.

In an eighth aspect of the first embodiment, x is 1 and M is H, $Na^+$ or $K^4$ and each of $R^2$, $R^4$, $R^7$ and $R^8$ is —$CH_2CH_2N(CH_2SO_3M)_2$.

In a ninth aspect of the first embodiment, x is 1 and M is $H^+$, $Na^+$ or $K^+$ and each of $R^2$, $R^3$, $R^4$, $R^7$ and $R^8$ is —$CH_2CH_2N(CH_2SO_3M)_2$;

In a tenth aspect of the first embodiment, the compositions described by any one of the 2nd to 9th aspects of the first embodiment is characterized in that the at least one polymixin or salt thereof is present in an amount of at least 10% by UHPLC, at least 20% by UHPLC, at least 30% by UHPLC, at least 40% by UHPLC, at least 50% by UHPLC, at least 60% by UHPLC, at least 70% by UHPLC, at least 80% by UHPLC, at least 90% by UHPLC, at least 95% by UHPLC, at least 97% by UHPLC, at least 98% by UHPLC, or at least 99% by UHPLC.

In an 11th aspect of the first embodiment, the at least one polymyxin or a salt thereof represented by formula (I) comprises more than 5 sulfomethyl groups.

In a 12th aspect of the first embodiment, the at least one polymyxin or a salt thereof represented by formula (I) comprises 6-10 sulfomethyl groups attached to γ-amino groups of the DAB residues.

In a 13th aspect of the first embodiment, the at least one polymyxin or a salt thereof represented by formula (I) comprises 6, 8 or 10 sulfomethyl groups attached to γ-amino groups on the DAB residues.

In a 14th aspect of the first embodiment, the at least one polymyxin or a salt thereof represented by formula (I) comprises 10 sulfomethyl groups attached to γ-amino groups on the DAB residues.

In a 15th aspect of the first embodiment, the at least one polymyxin or a salt thereof represented by formula (I) comprises 8 sulfomethyl groups attached to γ-amino groups on the DAB residues.

In a 16th aspect of the first embodiment, the at least one polymyxin or a salt thereof represented by formula (I) comprises 6 sulfomethyl groups attached to γ-amino groups on the DAB residues.

In a 17th aspect of the first embodiment, the at least one polymyxin or a salt thereof represented by formula (I) comprises 2 sulfomethyl groups attached to each of the five γ-amino groups on the DAB residues in polymyxin. Such polymyxins are deca sulfomethylated.

In an 18th aspect of the first embodiment, the at least one polymyxin or a salt thereof represented by formula (I) comprises 2 sulfomethyl groups attached to four of the γ-amino groups on DAB residues in polymyxin. Such polymyxins are octa sulfomethylated.

In a 19th aspect of the first embodiment, the at least one polymyxin or a salt thereof represented by formula (I) comprises 2 sulfomethyl groups attached to three of the γ-amino groups on DAB residues in polymyxin. Such polymyxins are hexa sulfomethylated.

Figure 4:
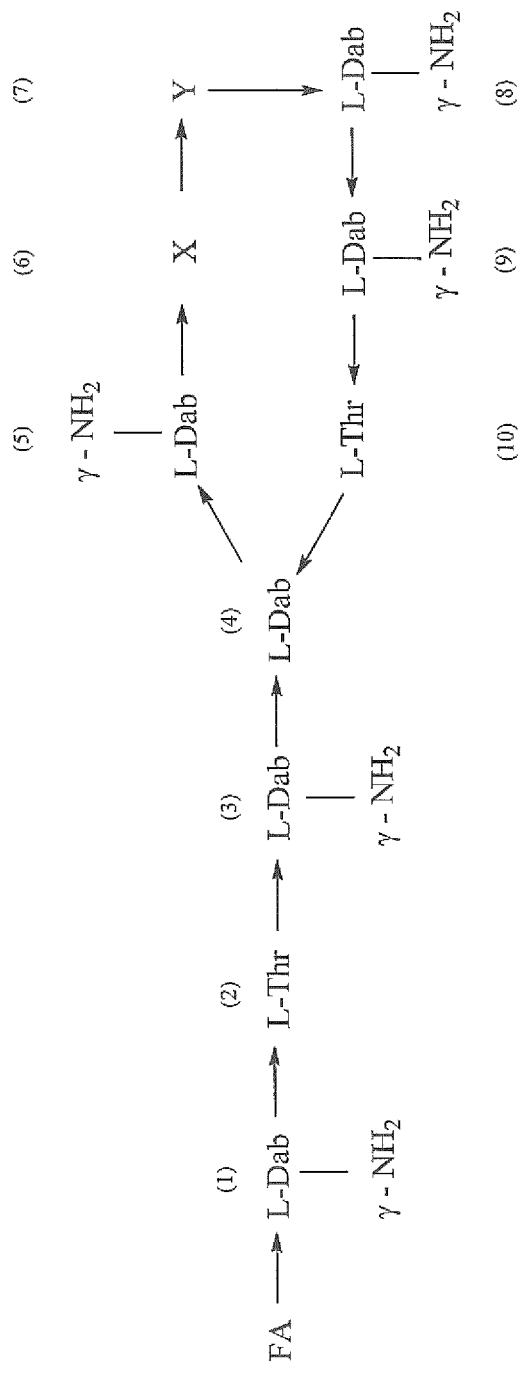
FIG. 4. A general chemical structure of some sulfomethylated polymyxins as described herein (cf Table 1).
Figure 5:
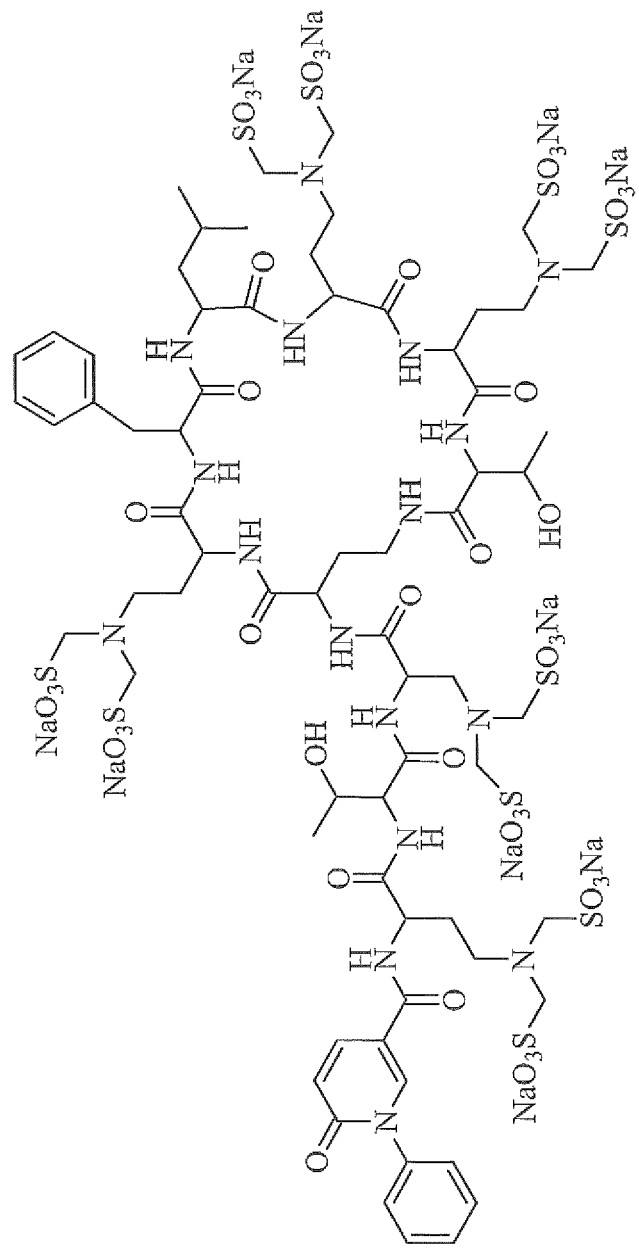
FIG. 5. Structure of a deca sulfomethylated polymyxin containing a DAP residue in position 3.

In a 20th aspect of the first embodiment, the at least one polymyxin or a salt thereof represented by formula (I) comprise 2 sulfomethyl groups attached to the γ-amino groups on DAB residues 1, 3, 5, 8 and 9, using the conventional polymyxin numbering system (FIG. 4.). Said polymyxin compound is designated herein as penta (Nγ-bis-sulfomethyl) DAB1,3,5,8,9 polymyxin. The structure for deca sulfomethylated Polymyxin E1 is shown in FIG. 1. and is given the abbreviated name PE1-(SM)101,3,5,8,9.

Figure 2:
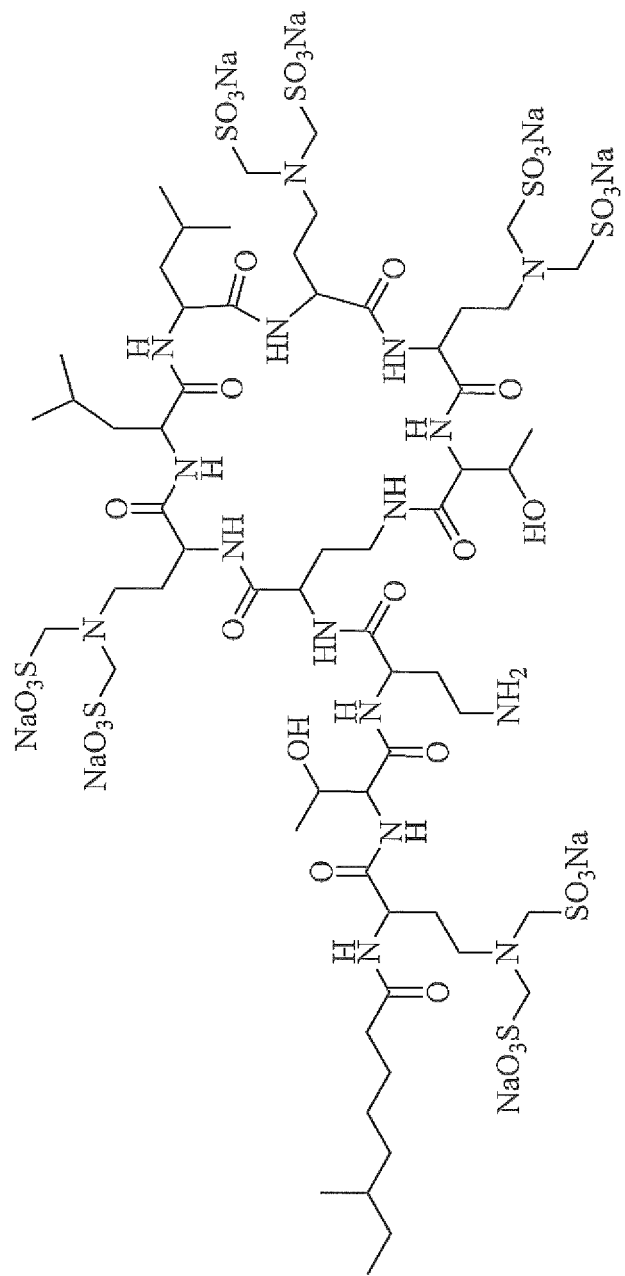
FIG. 2. Structure of PE1-$(SM)_8^{1,5,8,9}$.

In a 21st aspect of the first embodiment, the at least one polymyxin or a salt thereof represented by formula (I) comprises 2 sulfomethyl groups attached to the γ-amino groups on DAB residues 1, 5, 8 and 9, using the conventional polymyxin numbering system (FIG. 4). An example of said polymyxin compound is designated herein as tetra (Nγ-bis-sulfomethyl) DAB1,5,8,9 polymyxin E1. An example of such a compound is shown in FIG. 2. The abbreviated name for this compound is PE1-(SM)81,5,8,9.

Other examples of octa sulfomethylated polymyxins are tetra (Nγ-bis-sulfomethyl) DAB1,3,5,8 polymyxin E1, tetra (Nγ-bis-sulfomethyl) DAB1,3,8,9 polymyxin E1, tetra (Nγ-bis-sulfomethyl) DAB1,3,5,9 polymyxin E1, tetra (Nγ-bis-sulfomethyl) DAB3,5,8,9 polymyxin E1.

Figure 3:
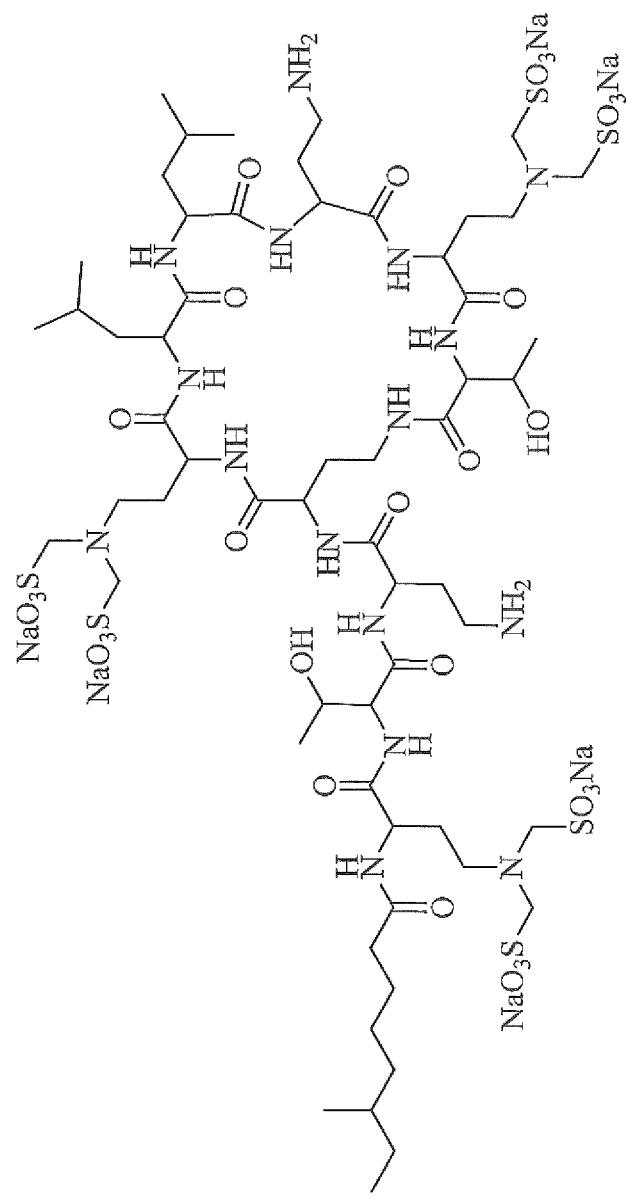
FIG. 3. Structure of PE1-$(SM)_6^{1,5,9}$.

In a 22nd aspect of the first embodiment, the at least one polymyxin or a salt thereof represented by formula (I) comprises 2 sulfomethyl groups attached to the γ-amino groups on DAB residues 1, 5, and 9. An example of said polymyxin is designated herein as tri (Nγ-bis-sulfomethyl) DAB1,5,9 polymyxin E1, the structure of which is shown in FIG. 3. An abbreviated name for this compound is PE1-(SM)61,5,9. Other examples of hexa sulfomethylated polymyxins are shown in Table 1.

TABLE 1

Examples of polymyxins which are penta, tetra and tri Nγ-bis-sulfomethylated

| | | DAB Position | | | | |
|---|---|---|---|---|---|---|
| | | 1 | 3 | 5 | 8 | 9 |
| (Nγ-bis-sulfomethyl) | Penta | x | x | x | x | x |
| | Tetra | x | x | x | x | — |
| | (5 different) | x | x | x | — | x |
| | | x | x | — | x | x |
| | | x | — | x | x | x |
| | | — | x | x | x | x |
| | Tri | x | x | x | — | — |
| | (10 Different) | x | x | — | — | x |
| | | x | — | — | x | x |
| | | — | — | x | x | x |
| | | — | x | x | x | — |
| | | — | x | — | x | x |
| | | x | — | x | — | x |

TABLE 1-continued

Examples of polymyxins which are penta,
tetra and tri N$^\gamma$-bis-sulfomethylated

| DAB Position | | | | |
|---|---|---|---|---|
| 1 | 3 | 5 | 8 | 9 |
| x | x | — | x | — |
| — | x | x | — | x |
| x | — | x | x | — |

Each x represents a bis-sulfomethylated DAB γ-amine.

Each x represents a bis-sulfomethylated DAB γ-amine.

In a 23rd aspect of the first embodiment, the at least one polymyxin or a salt thereof represented by formula (I) comprises sulfomethyl groups attached to the 7-amino groups on DAB residues 1, 3, 5, 8 and 9 in polymyxin E.

In a 24th aspect of the first embodiment, the at least one polymyxin or a salt thereof represented by formula (I) comprises 2 sulfomethyl groups attached to the 7-amino groups on DAB residues 1, 5, 8 and 9 in polymyxin E.

In a 25th aspect of the first embodiment, the at least one polymyxin or a salt thereof represented by formula (I) comprises 2 sulfomethyl groups attached to the 7-amino groups on DAB residues 1, 5, and 9 in polymyxin E.

In a 26th aspect of the first embodiment, the at least one polymyxin or a salt thereof represented by formula (I) is polymyxin E or a salt thereof.

In a 27th aspect of the first embodiment, the at least one polymyxin or a salt thereof represented by formula (I) is polymyxin B or a salt thereof.

In a 28th aspect of the first embodiment, the at least one polymyxin or a salt thereof represented by formula (I) has a purity of more than 10% based on UHPLC chromatogram.

In a 29th aspect of the first embodiment, the at least one polymyxin or a salt thereof represented by formula (I) has a purity of more than 20% based on UHPLC chromatogram.

In a 30th aspect of the first embodiment, the at least one polymyxin or a salt thereof represented by formula (I) has a purity of more than 30% based on UHPLC chromatogram.

In a 31st aspect of the first embodiment, the at least one polymyxin or a salt thereof represented by formula (I) has a purity of more than 40% based on UHPLC chromatogram.

In a 32nd aspect of the first embodiment, the at least one polymyxin or a salt thereof represented by formula (I) has a purity of more than 50% based on UHPLC chromatogram.

In a 33rd aspect of aspect of the first embodiment, the at least one polymyxin or a salt thereof represented by formula (I) has a purity of more than 60% based on UHPLC chromatogram.

In a 34th aspect of the first embodiment, the at least one polymyxin or a salt thereof represented by formula (I) has a purity of more than 70% based on UHPLC chromatogram.

In a 35th aspect of the first embodiment, the at least one polymyxin or a salt thereof represented by formula (I) has a purity of more than 80% based on UHPLC chromatogram.

In a 36th aspect of the first embodiment, the at least one polymyxin or a salt thereof represented by formula (I) has a purity of more than 90% based on UHPLC chromatogram.

In a 37th aspect of the first embodiment, the at least one polymyxin or a salt thereof represented by formula (I) has a purity of more than 95% based on UHPLC chromatogram.

In a 38th aspect of the first embodiment, the at least one polymyxin or a salt thereof represented by formula (I) comprises at least 10% w/w of at least one polymyxin or salt thereof comprising 6-10 sulfomethyl groups.

In a 39th aspect of the first embodiment, the at least one polymyxin or a salt thereof represented by formula (I) comprises at least 20% w/w of the at least one polymyxin or salt thereof comprising 6-10 sulfomethyl groups.

In a 40th aspect of the first embodiment, the at least one polymyxin or a salt thereof represented by formula (I) comprises at least 30% w/w of the at least one polymyxin or a salt thereof comprising 6-10 sulfomethyl groups.

In a 41st aspect of the first embodiment, the at least one polymyxin or a salt thereof represented by formula (I) comprises at least 40% w/w of the at least one polymyxin or salt thereof comprising 6-10 sulfomethyl groups.

In a 42nd aspect of the first embodiment, the at least one polymyxin or a salt thereof represented by formula (I) comprises at least 50% w/w of the least one polymyxin or salt thereof comprising 6-10 sulfomethyl groups.

In a 43rd aspect of the first embodiment, the at least one polymyxin or a salt thereof represented by formula (I) comprises at least 60% w/w of the at least one polymyxin or salt thereof comprising 6-10 sulfomethyl groups.

In a 44th aspect of the first embodiment, the at least one polymyxin or a salt thereof represented by formula (I) comprises at least 70% w/w of the at least one polymyxin or salt thereof comprising 6-10 sulfomethyl groups.

In a 45th aspect of the first embodiment, the at least one polymyxin or a salt thereof represented by formula (I) comprises at least 80% w/w of the at least one polymyxin or salt thereof comprising 6-10 sulfomethyl groups.

In a 46th aspect of the first embodiment, the at least one polymyxin or a salt thereof represented by formula (I) comprises at least 90% w/w of the at least one polymyxin or salt thereof comprising 6-10 sulfomethyl groups.

In a 47th aspect of the first embodiment, the at least one polymyxin or a salt thereof represented by formula (I) comprises at least 95% w/w of the at least one polymyxin or salt thereof comprising 6-10 sulfomethyl groups.

In a 48th aspect of the first embodiment the at least one polymyxin or salt thereof represented by formula (I) comprises any one of (A) to (J), wherein
(A) $R^1$ is 6-methyloctanoyl; each of $R^2$, $R^3$, $R^4$, $R^7$, and $R^8$ is —CH$_2$CH$_2$N(CH$_2$SO$_3$M)$_2$; and each of $R^5$ and $R^6$ is —CH$_2$CH(CH$_3$)$_2$;
(B) $R^1$ is 6-methyloctanoyl; each of $R^2$, $R^4$, $R^7$, and $R^8$ is —CH$_2$CH$_2$N(CH$_2$SO$_3$M)$_2$; $R^3$ is —CH$_2$CH$_2$NH$_2$; and each of $R^5$ and $R^6$ is —CH$_2$CH(CH$_3$)$_2$;
(C) $R^1$ is 6-methyloctanoyl; each of $R^2$, $R^4$, and $R^8$ is —CH$_2$CH$_2$N(CH$_2$SO$_3$M)$_2$; each of $R^3$ and $R^7$ is —CH$_2$CH$_2$NH$_2$; and each of $R^5$ and $R^6$ is —CH$_2$CH(CH$_3$)$_2$;
(D) $R^1$ is

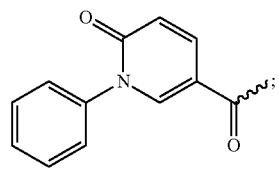

each of $R^2$, $R^4$, $R^7$, and $R^8$ is —CH$_2$CH$_2$N(CH$_2$SO$_3$M)$_2$; $R^3$ is —CH$_2$N(CH$_2$SO$_3$M)$_2$; $R^5$ is —CH$_2$C$_6$H$_5$; and $R^6$ is —CH$_2$CH(CH$_3$)$_2$;
(E) $R^1$ is 6-methylheptanoyl; each of $R^2$, $R^3$, $R^4$, $R^7$, and $R^8$ is —CH$_2$CH$_2$N(CH$_2$SO$_3$M)$_2$; and each of $R^5$ and $R^6$ is —CH$_2$CH(CH$_3$)$_2$;

(F) $R^1$ is 6-methyloctanoyl; each of $R^2$, $R^3$, $R^4$, $R^7$, and $R^8$ is —$CH_2CH_2N(CH_2SO_3M)_2$; $R^5$ is —$CH(CH_3)CH_2CH_3$; and $R^6$ is —$CH_2CH(CH_3)_2$;

(G)
(1) $R^1$ is 6-methyloctanoyl; each of $R^2$, $R^3$, $R^4$, $R^7$, and $R^8$ is —$CH_2CH_2N(CH_2SO_3M)_2$; each of $R^5$ and $R^6$ is —$CH_2CH(CH_3)_2$;
(2) $R^1$ is 6-methylheptanoyl; each of $R^2$, $R^3$, $R^4$, $R^7$, and $R^8$ is —$CH_2CH_2N(CH_2SO_3M)_2$; and each of $R^5$ and $R^6$ is —$CH_2CH(CH_3)_2$;
(3) $R^1$ is octanoyl; each of $R^2$, $R^3$, $R^4$, $R^7$, and $R^8$ is —$CH_2CH_2N(CH_2SO_3M)_2$; and each of $R^5$ and $R^6$ is —$CH_2CH(CH_3)_2$;
(4) $R^1$ is 6-methyloctanoyl; each of $R^2$, $R^3$, $R^4$, $R^7$, and $R^8$ is —$CH_2CH_2N(CH_2SO_3M)_2$; $R^5$ is —$CH(CH_3)CH_2CH_3$; and $R^6$ is —$CH_2CH(CH_3)_2$; and
(5) $R^1$ is 7-methyloctanoyl; each of $R^2$, $R^3$, $R^4$, $R^7$, and $R^8$ is —$CH_2CH_2N(CH_2SO_3M)_2$; and each of $R^5$ and $R^6$ is —$CH_2CH(CH_3)_2$;

(H)
(1) $R^1$ is 6-methyloctanoyl; each of R, $R^3$, $R^4$, $R^7$, and $R^8$ is —$CH_2CH_2N(CH_2SO_3M)_2$; $R^5$ is —$CH_2C_6H_5$; and $R^6$ is —$CH_2CH(CH_3)_2$;
(2) $R^1$ is 6-methylheptanoyl; each of $R^2$, $R^3$, $R^4$, $R^7$, and $R^8$ is —$CH_2CH_2N(CH_2SO_3M)_2$; $R^5$ is —$CH_2C_6H_5$; and $R^6$ is —$CH_2CH(CH_3)_2$;

(I) $R^1$ is 6-methyloctanoyl; each of $R^2$, $R^4$, $R^7$, and $R^8$ is —$CH_2CH_2N(CH_2SO_3M)_2$; $R^3$ is —$CH_2CH_2NH_2$; and each of $R^5$ and $R^6$ is —$CH_2CH(CH_3)_2$; and (J) $R^1$ is 6-methyloctanoyl; each of $R^2$, $R^4$, and R is —$CH_2CH_2N(CH_2SO_3M)_2$; each of $R^3$ and $R^7$ is —$CH_2CH_2NH_2$; and each of $R^5$ and $R^6$ is —$CH_2CH(CH_3)_2$.

In a 49th aspect of the first embodiment the at least one polymyxin or salt thereof represented by formula (I) comprises any one of (A) to (J), wherein (A) $R^1$ is 6-methyloctanoyl; each of $R^2$, $R^3$, $R^4$, $R^7$, and $R^8$ is —$CH_2CH_2N(CH_2SO_3Na)_2$; and each of $R^5$ and $R^6$ is —$CH_2CH(CH_3)_2$;
(B) $R^1$ is 6-methyloctanoyl; each of $R^2$, $R^4$, $R^7$, and $R^8$ is —$CH_2CH_2N(CH_2SO_3Na)_2$; $R^3$ is —$CH_2CH_2NH_2$; and each of $R^5$ and $R^6$ is —$CH_2CH(CH_3)_2$;
(C) $R^1$ is 6-methyloctanoyl; each of $R^2$, $R^4$, and $R^8$ is —$CH_2CH_2N(CH_2SO_3Na)_2$; each of $R^3$ and $R^7$ is —$CH_2CH_2NH_2$; and each of $R^5$ and $R^6$ is —$CH_2CH(CH_3)_2$;
(D) $R^1$ is

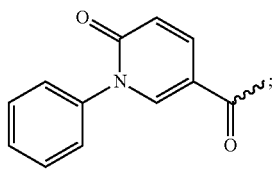

each of $R^2$, $R^4$, $R^7$, and $R^8$ is —$CH_2CH_2N(CH_2SO_3Na)_2$; $R^3$ is —$CH_2N(CH_2SO_3Na)_2$; $R^5$ is —$CH_2C_6H_5$; and $R^6$ is —$CH_2CH(CH_3)_2$;
(E) $R^1$ is 6-methylheptanoyl; each of $R^2$, $R^3$, $R^4$, $R^7$, and R is —$CH_2CH_2N(CH_2SO_3Na)_2$; and each of $R^5$ and $R^6$ is —$CH_2CH(CH_3)_2$;
(F) $R^1$ is 6-methyloctanoyl; each of $R^2$, $R^3$, $R^4$, $R^7$, and $R^8$ is —$CH_2CH_2N(CH_2SO_3Na)_2$; $R^5$ is —$CH(CH_3)CH_2CH_3$; and $R^6$ is —$CH_2CH(CH_3)_2$;

(G)
(1) $R^1$ is 6-methyloctanoyl; each of $R^2$, $R^3$, $R^4$, $R^7$, and $R^8$ is —$CH_2CH_2N(CH_2SO_3Na)_2$; each of $R^5$ and $R^6$ is —$CH_2CH(CH_3)_2$;
(2) $R^1$ is 6-methylheptanoyl; each of $R^2$, $R^3$, $R^4$, $R^7$, and $R^8$ is —$CH_2CH_2N(CH_2SO_3Na)_2$; and each of $R^5$ and $R^6$ is —$CH_2CH(CH_3)_2$;
(3) $R^1$ is octanoyl; each of $R^2$, $R^3$, $R^4$, $R^7$, and $R^8$ is —$CH_2CH_2N(CH_2SO_3Na)_2$; and each of $R^5$ and $R^6$ is —$CH_2CH(CH_3)_2$;
(4) $R^1$ is 6-methyloctanoyl; each of $R^2$, $R^3$, $R^4$, $R^7$, and $R^8$ is —$CH_2CH_2N(CH_2SO_3Na)_2$; $R^5$ is —$CH(CH_3)CH_2CH_3$; and $R^6$ is —$CH_2CH(CH_3)_2$; and
(5) $R^1$ is 7-methyloctanoyl; each of $R^2$, $R^3$, $R^4$, $R^7$, and $R^8$ is —$CH_2CH_2N(CH_2SO_3Na)_2$; and each of $R^5$ and $R^6$ is —$CH_2CH(CH_3)_2$;

(H)
(1) $R^1$ is 6-methyloctanoyl; each of $R^2$, $R^3$, $R^4$, $R^7$, and $R^8$ is —$CH_2CH_2N(CH_2SO_3Na)_2$; $R^5$ is —$CH_2C_6H_5$; and $R^6$ is —$CH_2CH(CH_3)_2$;
(2) $R^1$ is 6-methylheptanoyl; each of $R^2$, $R^3$, $R^4$, $R^7$, and $R^8$ is —$CH_2CH_2N(CH_2SO_3Na)_2$; $R^5$ is —$CH_2C_6H_5$; and $R^6$ is —$CH_2CH(CH_3)_2$;

(I) $R^1$ is 6-methyloctanoyl; each of $R^2$, $R^4$, $R^7$, and $R^8$ is —$CH_2CH_2N(CH_2SO_3Na)_2$; $R^3$ is —$CH_2CH_2NH_2$; and each of $R^5$ and $R^6$ is —$CH_2CH(CH_3)_2$; and (J) $R^1$ is 6-methyloctanoyl; each of $R^2$, $R^4$, and $R^8$ is —$CH_2CH_2N(CH_2SO_3Na)_2$; each of $R^3$ and $R^7$ is —$CH_2CH_2NH_2$; and each of $R^5$ and $R^6$ is —$CH_2CH(CH_3)_2$.

In a 50th aspect of the first embodiment the at least one polymyxin is represented by the structure as shown in FIG. 1, FIG. 2, FIG. 3, FIG. 5, FIG. 7 or FIG. 8.

Figure 9:
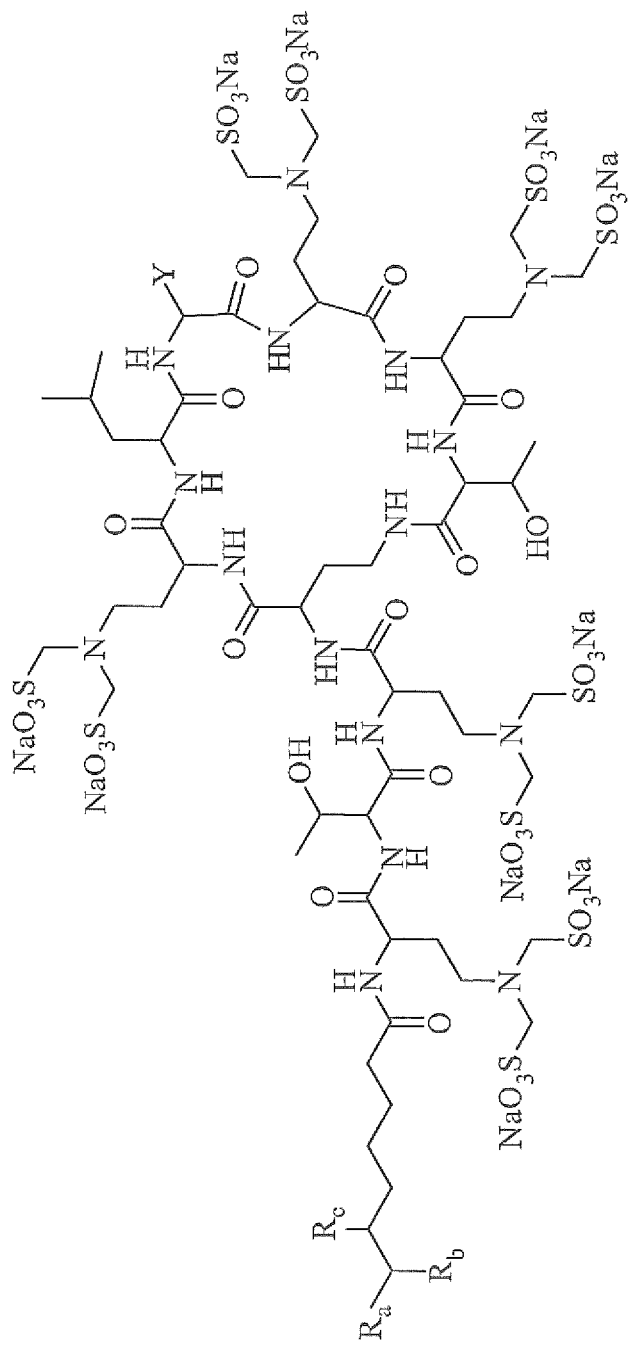
FIG. 9. Structure of polymyxin components in PE-$(MS)_{10}^{1,3,5,8,9}$ composition described in Example 4.
Figure 10:
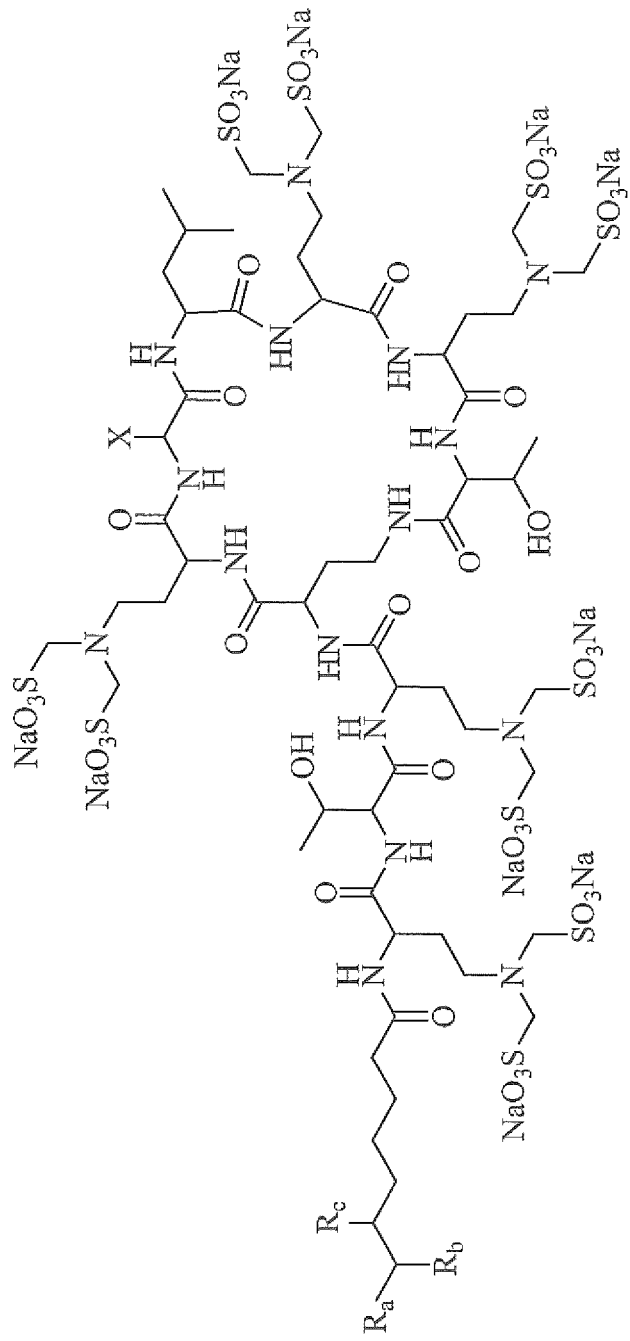
FIG. 10. Structure of polymyxin components in PB-$(MS)_{10}^{1,3,5,8,9}$ composition described in Example 5.

In a 51th aspect of the first embodiment the composition comprises polymyxins represented by the structures as shown in FIG. 9 or FIG. 10.

Polymyxins are antibiotic decapeptides containing a heptapeptide ring and an N-terminal amide coupled fatty acid. Several polymyxins are naturally produced by *Bacillus polymyxa*. The structure and history of polymyxins is known and is described, for example, by Velkov et al. J. Med. Chem. (2010) 53(5): 1898-1916.

The polymyxins as described herein embrace many molecular species with respect to number of substituents and their positions. For example in aqueous solutions, the charge will depend on pH. The polymyxins compounds as described herein cover all pharmaceutical acceptable salts and ions thereof. Among such polymyxins are of course the hexa-, octa-, and deca-sodium salts. Other pharmaceutically acceptable salts are also included e.g. potassium, lithium, and ammonium salts (such as $HmN(C_{1-4}alkyl)n+$ where m is 0-4 and n is 0-4 with the proviso that m+n=4), or combinations thereof.

The polymyxins as described herein comprise any polymyxin compound having 6-10 sulfomethyl groups attached to γ-amino groups on DAB residues.

The numbering of residues in polymyxins is according to Velkov et al, see, e.g., FIG. 4. In naturally occurring polymyxins, the fatty acid is attached to the N-terminal amino acid residue 1 and the amino acid residue (10) forms a lariate structure with amino acid residue (4). In other words the fatty acyl group (such as, 6-methyl-heptanoic or the 6-methyl-octanoic acid) is amide-coupled to I-DAB residue (1) and threonine residue (10) is amide coupled to 1-DAB residue (4) in some naturally occurring polymyxins.

The only difference in the structure between polymyxin B and polymyxin E (colistin) lies in the amino acid components. Polymyxins contain mainly L-amino acids arranged as a cyclic heptapeptide ring with a tripepetide side chain, with the side chain covalently bound to a fatty acid. (See, e.g., FIG. 4.) The difference between polymyxin B and polymyxin E is in residue 6. In polymyxin B residue (6) is D-phenylalanine and in polymyxin E residue (6) is D-leucine, both containing 1-leucine at residue (7).

It will be appreciated that the stereochemical designations identified in FIG. 4. are not meant to limit the possible stereochemical designations of the carbon-based stereocenters that are present in the at least one polymyxin or a salt thereof represented by formula (I).

Certain polymyxin derivatives embraced by the at least one polymyxin or a salt thereof represented by formula (I) include the at least one polymyxin or salt thereof comprising 6-10 sulfomethyl groups attached to γ-amino groups on 1-DAB residues or the β-amino groups on 1-DAP residues, as described in WO 2012/168820, which corresponds to US 2012/0316105. Therein the compounds do not contain 6-10 sulfomethyl groups. One example of the at least one polymyxin or a salt thereof represented by formula (I) include the compound having the following structure:

TABLE 2

Examples of sulfomethylated polymyxins

| Sulfomethylated polymyxins | Abbr. | FA | Dab 1 (N$^\gamma$) | Dab 3 (N$^\gamma$) | Dab 5 (N$^\gamma$) | X 6 | Y 7 | Dab 8 (N$^\gamma$) | Dab 9 (N$^\gamma$) |
|---|---|---|---|---|---|---|---|---|---|
| penta (N$^\gamma$-bis-sulfomethyl) DAB$^{1,3,5,8,9}$ Polymyxin E1 | PE1-(SM)$_{10}$$^{1,3,5,8,9}$ | 6-MOA | 2SM | 2SM | 2SM | Leu | Leu | 2SM | 2SM |
| penta (N$^\gamma$-bis-sulfomethyl) DAB$^{1,3,5,8,9}$ Polymyxin E2 | PE2-(SM)$_{10}$$^{1,3,5,8,9}$ | 6-MHA | 2SM | 2SM | 2SM | Leu | Leu | 2SM | 2SM |
| penta (N$^\gamma$-bis-sulfomethyl) DAB$^{1,3,5,8,9}$ Polymyxin E1-i | PE1-i-(SM)$_{10}$$^{1,3,5,8,9}$ | 6-MOA | 2SM | 2SM | 2SM | Leu | Ile | 2SM | 2SM |
| penta (N$^\gamma$-bis-sulfomethyl) DAB$^{1,3,5,8,9}$ Colistin | PE-(SM)$_{10}$$^{1,3,5,8,9}$ | 6-MOA/ 6-MHA/ 6-OCT | 2SM | 2SM | 2SM | Leu | Leu/Ile | 2SM | 2SM |
| penta (N$^\gamma$-bis-sulfomethyl) DAB$^{1,3,5,8,9}$ Polymyxin B | PB-(SM)$_{10}$$^{1,3,5,8,9}$ | 6-MOA/ 6-MHA/ 6-OCT | 2SM | 2SM | 2SM | Phe | Leu | 2SM | 2SM |
| tetra (N$^\gamma$-bis-sulfomethyl) DAB$^{1,5,8,9}$ Polymyxin E1 | PE1-(SM)$_8$$^{1,5,8,9}$ | 6-MOA | 2SM | 2H | 2SM | Leu | Leu | 2SM | 2SM |
| tri (N$^\gamma$-bis-sulfomethyl) DAB$^{1,5,9}$ Polymyxin E1 | PE1-(SM)$_6$$^{1,5,9}$ | 6-MOA | 2SM | 2H | 2SM | Leu | Leu | 2H | 2SM |

(FA = Fatty acyl, 6-MOA = 6-methyloctanoyl, 6-MHA = 6-methylheptanoyl, 6-OCT = Octanoyl, 2SM = bis-sulfomethyl, Leu = Leucine residue, Ile = Isoleucine residue, Phe = Phenylalanine residue, DAB1 = DAB residue number 1 etc.)

Many of the naturally occurring polymyxins comprise 6-methyl-heptanoic or the 6-methyl-octanoic acid coupled to the peptide by an amide bond. Numerous polymyxins with natural fatty acids exchanged with synthetic fatty acids have been produced in the prior art. The polymyxins of the present invention are also meant to embrace such semisynthetic polymyxins if they otherwise fulfill the features of the claims. For example, many semisynthetic polymyxins are described in the literature, see, e.g., Magee et al. J. Med. Chem. (2013) 56: 5079-5093.

The term "CMS" as described herein refers to a composition comprising sulfomethylated polymyxin E1 and sulfomethylated polymyxin E2. Chemical abstracts have assigned such a composition the number 8068-28-8 for CMS.

The term "colistin" as described herein refers to a composition comprising polymyxin E1 and polymyxin E2. Chemical abstracts have assigned the number 1066-17-7 for colistin. According to EP pharmacopoeia, colistin should comprise more than 77% of Polymyxin E1, E2, E3, Eli and E1-7MOA, but less than 10% of each of the minor components Polymyxin E3, E1-i and E1-MOA.

The term "Polymyxin E" as described herein is used interchangeably with "colistin".

The term "Polymyxin E1" as described herein refers to the compound having the CAS no 7722-44-3. Polymyxin E1 is used interchangeably with colistin A.

The term "Polymyxin E2" as described herein refers to the compound having the CAS no 7239-48-7. Polymyxin E2 is used interchangeably with colistin B.

The expression "sulfomethylated polymyxin" as described herein refers to a polymyxin comprising at least one sulfomethyl group attached to a γ-amino group on an 1-DAB residue.

A second embodiment is directed to a pharmaceutical composition comprising an effective amount of any one of the compositions described in the numerous aspects of the first embodiment.

In a first aspect of the second embodiment, the pharmaceutical composition further comprises a pharmaceutically acceptable excipient. The pharmaceutically acceptable excipient may include a preservative, a buffer, an antioxidant, or a diluent. Suitable diluents include, but are not limited to Diluents: water for injection, 0.9% NaCl, 5% dextrose in 0.9% NaCl, 5% dextrose in water, 5% dextrose in 0.45% NaCl, 5% dextrose in 0.225% NaCl, and Lactated Ringer's solution.

The pharmaceutical composition may be a lyophilized product capable of being reconstituted using a suitable diluent for administration by an injectable route (e.g., either parenteral or intravenous administration) or by inhalation using for example a nebulizer or other such inhalation device.

The term "effective amount" as used herein means an amount required to reduce symptoms of a bacterial infection, such as a gram-negative bacterial infection, such as, e.g., *Pseudomonas aeruginosa, Acinetobacter baumannii, Klebsiella pneumoniae, Escherichia coli, Enterobacter aerogenes*, etc.) in a subject. The dose will be adjusted to the individual requirements in each particular case. That dosage can vary within wide limits depending upon numerous factors such as the severity of the disease to be treated, the age and general health condition of the patient, other medicaments with which the patient is being treated, the route and form of administration and the preferences and experience of the medical practitioner involved.

A third embodiment is directed to a use of a pharmaceutical composition comprising an effective amount of any one of the compositions described in the numerous aspects of the first embodiment in treating a gram-negative bacterial infection.

In a first aspect of the third embodiment, the use is the same for commercially available polymyxin drug products, such as, for example, Colistimethate for Injection, USP.

In a second aspect of the third embodiment, the use is for the treatment of infections caused or mediated by *Pseudomonas aeruginosa, Acinetobacter baumannii, Klebsiella pneumoniae, Escherichia coli, Enterobacter aerogenes*, or a combination thereof.

A fourth embodiment is directed to a method of treating a gram-negative bacterial infection in an infected patient, which comprises administering to the patient a pharmaceutical composition comprising an effective amount of any one of the compositions described in the numerous aspects of the first embodiment.

In a first aspect of the fourth embodiment, the method of treatment is substantially the same as the indicated use for commercially available polymyxin drug products, such as, for example, Colistimethate for Injection, USP.

In a second aspect of the fourth embodiment, the gram-negative bacterial infection is caused or mediated by *Pseudomonas aeruginosa, Acinetobacter baumannii, Klebsiella pneumoniae, Escherichia coli, Enterobacter aerogenes*, or a combination thereof.

A fifth embodiment is directed to a method of treating a gram-negative bacterial infection in an infected patient, which comprises administering to the patient a pharmaceutical composition comprising an effective amount of any one of the compositions described in the numerous aspects of the first embodiment in combination with another anti-bacterial agent.

In a first aspect of the fifth embodiment, administration of the pharmaceutical composition and another anti-bacterial agent is performed concurrently or alternatively with no particular temporal order of administration.

In a second aspect of the fifth embodiment, the gram-negative bacterial infection is caused or mediated by *Pseudomonas aeruginosa, Acinetobacter baumannii, Klebsiella pneumoniae, Escherichia coli, Enterobacter aerogenes*, or a combination thereof.

A sixth embodiment is directed to a process for preparing any one of the compositions described in the numerous aspects of the first embodiment, which comprises:

reacting a compound or salt thereof for formula II with a methylsulfonation reagent

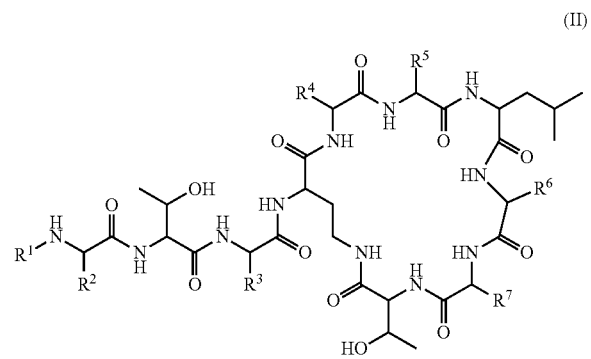

(II)

wherein $R^1$ is an aliphatic linear or branched $C_6$-$C_{10}$ acyl group, or

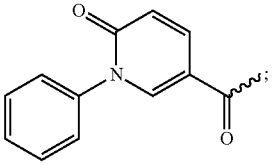

$R^5$ is —$CH(CH_3)_2$, —$CH_2CH(CH_3)_2$, —$CH(CH_3)CH_2CH_3$, or —$CH_2C_6H_5$;

$R^6$ is —$CH(CH_3)_2$, —$CH_2CH(CH_3)_2$, or —$CH(CH_3)CH_2CH_3$;

each of $R^2$, $R^3$, $R^4$, $R^7$ and $R^8$ is —$(CH_2)_xCH_2NH_2$; and wherein x is 0 or 1.

A seventh embodiment is directed to a product obtained by a process as described in the fifth embodiment.

Materials and Methods

Ultra High Pressure Liquid Chromatography (UHPLC):

The UHPLC method used was a Waters Acquity system equipped with a quaternary pump system with a UV detector. The column used was a Waters Acquity UPLC CSH C18, 1.7 m, 150×2.1 mm kept at 30° C. All chromatograms were recorded using Empower 2. The flow rate was 0.30 mL/min and injection volume was 2 µL. The mobile phases consisted of; A) 0.05 M phosphate buffer pH 6.5 and acetonitrile (MeCN) in ratio 95:5 v/v B) 0.05 M phosphate buffer pH 6.5 and MeCN in ratio 50:50 v/v. All solvents and chemicals were of analytical grade and were filtered through a 0.2 µm filter prior to use. The gradient used was; Initial, 20% B; 0-10 min, linear to 32% B; 10-35 min, linear to 47% B; 35-36 min, linear to 20% B; 36 min-44 min, 20% B. All chromatograms were recorded at 210 nm. All solvents and chemicals were purchased from Merck, Germany, were of analytical or pro analysis (PA) grade.

Preparation of Test Sample Solution for UHPLC and MS

Samples were prepared by dissolving the CMS working standard in water, directly followed by dilution with methanol (MeOH) so that the final concentration of the samples were 2 mg/mL and the water content was 5%. This increases the sample stability by decreasing the hydrolysis of the sulfomethylated compounds. Identification of individual components was performed by dissolving the isolated component in pure methanol at a concentration of approximately 1 mg/mL. All samples were stored in fridge or autosampler at 2-8° C. prior to use.

Mass Spectrometry (MS)

All samples were analyzed by an electrospray infusion time-of-flight mass spectrometer (ESI-TOF MS) (Bruker microTOF) in negative mode. Samples were dissolved in methanol to a concentration of 0.5 mg/mL and put on ultrasonic bath for 30 min. The samples were infused at a flow rate of 250 µL/hour for approximately 30 seconds. The MS settings were; End Plate Offset –500 V, Capillary 3500V, Nebulizer 3.0 Bar, Dry Gas, 4.0 mL/min at 250° C., Capillary Exit varied from –80V to 120 V with a general value of –100.0V, Skimmer 1 –33.3 V, Hexapole 1 –23.5 V, Hexapole RF 300.0 Vpp, Skimmer 2 –223.5 V. The capillary exit significantly affects the fragmentation of the components. Optimization of this parameter for the individual components was therefore necessary. Some fragmentation was still seen for some of the compounds. Due to presence of misc. salts, in source decomposition, and other components, the MS spectra are not pure and may contain additional signals. However, since each component was isolated as a monocomponent (verified by UHPLC) it was expected that the highest possible mass was the intact molecule and all other masses with lower mass were fragments. This was also verified by varying the capillary exit energy.

NMR: The experiments were obtained using a Bruker 600 MHz spectrometer under standard pulse sequences for 1D and 2D NMR experiments. Data was recorded in $CD_3OH$ at 298 K Chemical shifts are reported in ppm relative to $CHD_2OH$ ($\delta_H$ 3.30 ppm) and $CD_3OH$ ($\delta_C$ 49.0 ppm. The following NMR experiments were acquired: $^1H$, $^{13}C$, DEPT, COSY, HMBC, HSQC, TOCSY and NOESY. The $^{15}N$ chemical shifts were referenced using frequency ratios as described by Wishart et al. J. Biomol. NMR (1995) 6: 135-140).

EXAMPLES

Not to be limited by way of example, the following examples serve to facilitate a better understanding of the subject matter disclosed herein.

Example 1

Preparation of Penta (Nγ-Bis-Sulfomethyl) DAB1,3,5,8,9 Polymyxin E1 (PE1-(SM)101,3,5,8,9 (FIG. 1))

Isolated polymyxin E1 sulfate (3.5 g) and a 45% w/w aqueous solution of formaldehyde sodium bisulfite (11.3 g) adduct were mixed and warmed to 60° C. while stirring. pH was then kept at 7.0-7.5 by several additions of 2 M NaOH. After 18 h the mixture was cooled to ambient temperature and the crude product furnished as a white solid by precipitation in 200 mL of methanol/acetonitrile 1/1 v/v.

The product was de-salted and polished by the following procedure: A C18 column 6μ e.g. Phenomenex X Bridge Prep Shield 10×250 mm or similar was washed and equilibrated with 5% MeCN (no salt). The column was mounted in a Waters Delta Prep HPLC system, 150 mL/min maximum flow. The detector was a Waters 2487 adjusted to 280 nm. A mixture of 9 mL 5% MeCN solution of 230 mg PE1-(SM)101,3,5,8,9 and 1 mL 2M NaCl was loaded the column and the flow was 6-8 mL/min.

Elute and desalt with 5% MeCN with 6-8 mL/min and collect the PE1-(SM)101,3,5,8,9 fraction. Some degradation occurred on-column during the process, but by cutting the head and tail off, the high purity will be maintained. The Head Fraction, ca 35 mL, was collected directly into 450 mL 100% MeCN and further 550 mL 100% MeCN was added before vacuum-evaporation of the 97:3 MeCN:H2O solution in a 2 L pear shaped evaporation flask. The distillation process was performed with a Büchi Rotavapor. The 94:6 azeotrope distills off making a water free PE1-(SM)101,3, 5,8,9 residue in the 2 L vacuum-distillation flask. The residue was removed with 3×8 mL 100% MeOH (dry) and poured into a 50 mL vacuum-evaporation flask and vacuum-evaporated to a 1-2 mL MeOH-PE1-(SM)101,3,5,8,9 suspension. 15 mL 100% MeCN was added and the solution/suspension was vacuum-evaporated further to dryness with a water bath temperature of 35° C. The pressure was decreased from 70-60 Torr down to 20-15 Torr during the process. Further vacuum-drying was done for 30 min with slow rotation in the 35° C. water bath with maintained vacuum. The yield was 150 mg substance of the PE1-(SM) 101,3,5,8,9. Several runs were performed to give 990 mg batch with a relative chromatographic purity higher than 90%.

Figure 6:
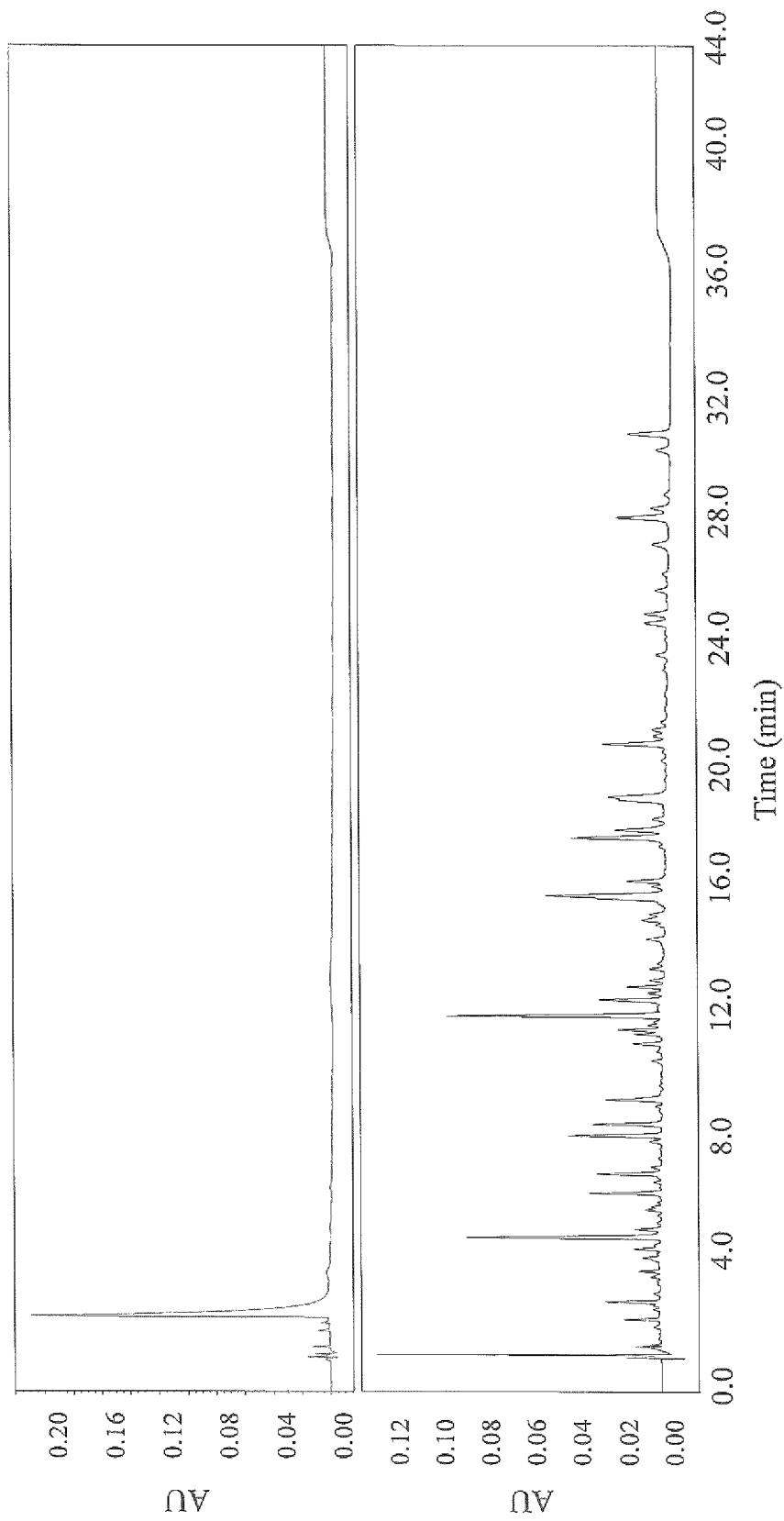
FIG. 6. UHPLC Chromatograms of PE1-$(SM)_{10}^{1,3,5,8,9}$ (FIG. 1, top) and CMS working standard (bottom).
Figure 7:
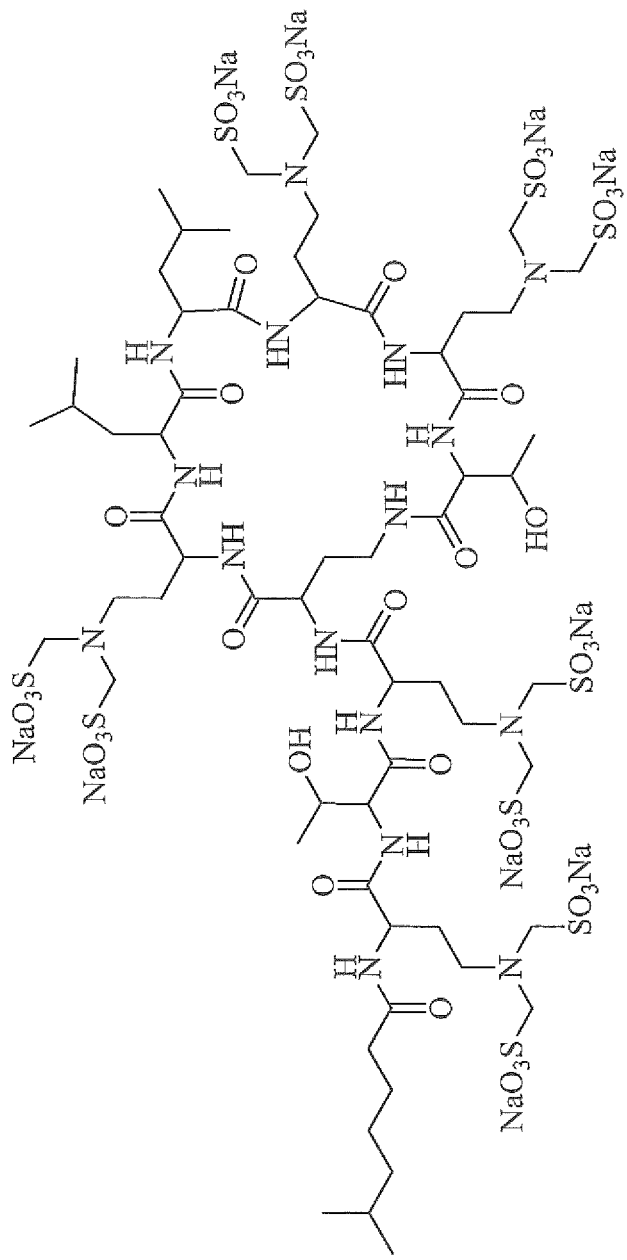
FIG. 7. Structure of PE2-$(SMI)_{10}^{1,3,5,8,9}$.
Figure 8:
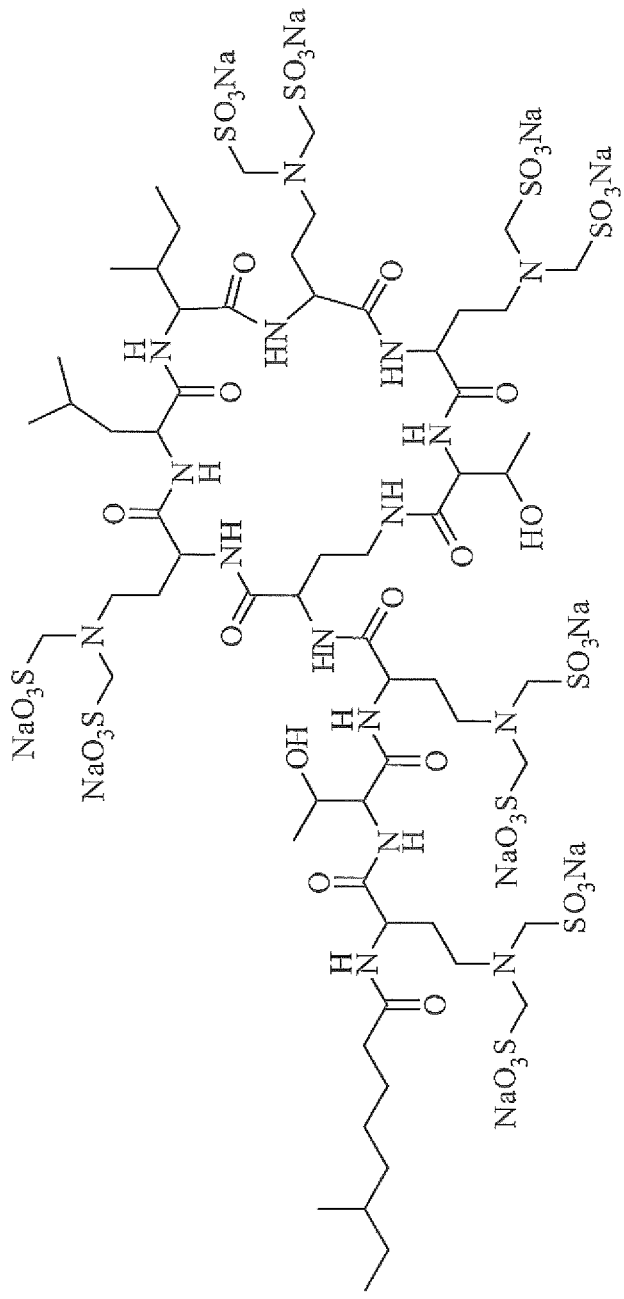
FIG. 8. Structure of PE1-i-$(SM)_{10}^{1,3,5,8,9}$.

UHPLC with gradient on reverse phase (CSH C18, 1.7 m, 150×2.1 mm) showed a single peak, with PE1-(SM)101,3, 5,8,9, C63H110N16Na10O43S10. The purity was 93% when the column eluent was monitored at 210 nm—see FIG. 6. Analysis was also performed through direct infusion of isolated component using ESI-TOF MS (negative mode): calc. m/z for C63H110N16Na10O43S10 [M]=2328.3. Found [M+8 Na]-2: m/z 1141.2 and [M+7Na]-3 m/z 753.1. The product was determined by 1H-, 13C, and 15N-NMR spectroscopy (data not shown).

Example 2

Preparation of Penta (Nγ-Bis-Sulfomethyl) DAB1,3,5,8,9 Polymyxin E2 (PE2-(SM)101,3,5,8,9 (FIG. 7))

Polymyxin E2 sulfate (3.5 g) and a 45% w/w aqueous solution of formaldehyde sodium bisulfite (11.3 g) adduct were mixed and warmed to 60° C. while stirring. pH was then kept at 7.0-7.5 by several additions of 2M NaOH. After 18 h the mixture was cooled to ambient temperature and the crude product furnished as a white solid by precipitation in 200 mL of methanol/acetonitrile 1/1 v/v. The product was further desalted and polished as described in Example 1.

UHPLC with gradient on reverse phase (CSH C18, 1.7 μm, 150×2.1 mm) showed a single peak, with PE2-(SM) 101,3,5,8,9, C62H108N16Na10O43S10. The purity was 81% when the column eluent was monitored at 210 nm. Analysis was also performed through direct infusion of isolated component using ESI-TOF MS (negative mode): calc. m/z for C62H108N16Na10O43S10 [M]=2314.5. Found [M+8 Na]-2: m/z 1135.2 and [M+7Na]-3: m/z 748.5. The product was determined by NMR spectroscopy.

Example 3

Preparation of Penta (Nγ-Bis-Sulfomethyl) DAB1,3,5,8,9 Polymyxin E1-i (PE1-i-(SM10)1,3,5,8,9 (FIG. 8))

Polymyxin E1-i sulfate (3.5 g) and a 45% w/w aqueous solution of formaldehyde sodium bisulfite (11.3 g) adduct were mixed and warmed to 60° C. while stirring. pH was then kept at 7.0-7.5 by several additions of 2M NaOH. After 18 h the mixture was cooled to ambient temperature and the crude product furnished as a white solid by precipitation in 200 mL of methanol/acetonitrile 1/1 v/v. The product was further desalted and polished as described in Example 1.

UHPLC with gradient on reverse phase (CSH C18, 1.7 μm, 150×2.1 mm) showed a single peak, with PE1-i-(SM) 10, C63H110N16Na10O43S10. The purity was 95% when the column eluent was monitored at 210 nm. Analysis was also performed through direct infusion of isolated component using ESI-TOF MS (negative mode): Found [M+8 Na]-2: m/z 1141.2 and [M+7Na]-3: m/z 753.1.

Example 4

Preparation of Penta (Nγ-Bis-Sulfomethyl) DAB1,3,5,8,9 Polymyxin E (PE-(SM)10)1,3,5,8,9 (FIG. 9)

Colistin sulfate mixture (3.5 g) and a 45% w/w aqueous solution of formaldehyde sodium bisulfite (11.3 g) adduct were mixed and warmed to 60° C. while stirring. pH was then kept at 7.0-7.5 by several additions of 2M NaOH. After 18 h the mixture was cooled to ambient temperature and the crude product furnished as a white solid by precipitation in 200 mL of methanol/acetonitrile 1/1 v/v. The products; PE-(SM)101,3,5,8,9 (FIG. 9) were further desalted and polished as described in Example 1.

UHPLC with gradient on reverse phase (CSH C18, 1.7 µm, 150×2.1 mm) showed a single peak for each major component of polymyxins, abbreviated PE-(SM)101,3,5,8, 9. The total relative purity of the 5 major polymyxin peaks was 83% when the column eluent was monitored at 210 nm. Analysis was also performed through direct infusion of the PE-(SM)101,3,5,8,9 mixture using ESI-TOF MS in negative mode calculated for the main components calc. m/z for E1: $C_{63}H_{110}N_{16}Na_{10}O_{43}S_{10}$ [M]=2328.3 and m/z for E2: $C_{62}H_{108}N_{16}Na_{10}O_{43}S_{10}$ [M]=2314.5. Found [M+8 Na]-2: m/z 1141.2+1135.1 and [M+7Na]-3: m/z 748.5 and 753.1, respectively.

Example 5

Preparation of Penta (Nγ-Bis-Sulfomethyl) DAB1,3,5,8,9 Polymyxin B (PB-(SM)10)1,3,5,8,9 (FIG. 10))

Polymyxin B sulfate (3.5 g) and a 45% w/w aqueous solution of formaldehyde sodium bisulfite (11.3 g) adduct were mixed and warmed to 60° C. while stirring. pH was then kept at 7.0-7.5 by several additions of 2M NaOH. After 18 h the mixture was cooled to ambient temperature and the crude product furnished as a white solid by precipitation in 200 mL of methanol/acetonitrile 1/1 v/v. The products; PB-(SM)101,3,5,8,9 (FIG. 10.) were further desalted and polished as described in Example 1.

UHPLC with gradient on reverse phase (CSH C18, 1.7 µm, 150×2.1 mm) showed the PB-(SM)101,3,5,8,9. Analysis was also performed through direct infusion of the PMB-(SM)101,3,5,8,9 mixture using ESI-TOF MS (negative mode) calculated for the main components calc. m/z for B1: $C_{66}H_{108}N_{16}Na_{10}O_{43}S_{10}$ [M]=2362.3 and m/z for B2: $C_{65}H_{106}N_{16}Na_{10}O_{43}S_{10}$ [M]=2348.3. Found M-2: m/z 1158.2+1151.2, and M-3 m/z 764.4 and 759.8 as major components (mixture of Polymyxin B components for each found mass).

Example 6

Antibacterial activity of deca sulfomethylated polymyxins against *Acinetobacter baumannii, Klebsiella pneumonia, Pseudomonas aeruginosa* and *Escherichia coli*.

The deca sulfomethylated polymyxins were tested for antibacterial activity by determining the minimal inhibitory concentration (MIC) by use of the broth dilution method according to EUCAST. 4 bacterial indicator organism were used e.g. *Acinetobacter baumannii* colistin-sensitive, *Klebsiella pneumonia* #3010, *Pseudomonas aeruginosa* ATCC27853, *Escherichia coli* ATCC25922 and *Escherichia coli* DSA443. The tests were performed at, Statens Serum Institut, Copenhagen, Denmark department for Microbiology and Infection Control.

The concentration range used was 0.125-128 µg/mL. Gentamicin was included as a positive quality control. Preparation of Gentamicin: 1000 µg/mL stock solution: 0.125 ml of a 40 mg/mL solution of Hexamicin+4.875 mL sterile water. 128 µg/mL: 0.640 mL of "1000 µg/mL stock solution"+4.36 mL Müeller-Hinton broth (MHB).

Preparation of compounds disclosed herein: 5 mg/ml stock solution: one vial of 5 mg was added 1.0 mL sterile water. 512 µg/mL solution: 0.205 mL of "5 mg/mL stock solution"+1.795 mL MHB Preparation of inoculum: Fresh overnight colonies from 5% horse blood agar plates were suspended to a turbidity of 0.5 McFarland and further diluted in Müeller-Hinton broth to 1×106 CFU/ml. A total of 50 µL diluted bacterial suspension (Müeller Hinton BBL II-broth, SSI) was added to wells containing 50 µL of two fold compounds described herein or gentamicin dilutions. All compounds were tested in triplicate. The plates were incubated at 35° C., 16-20 h.

The results are shown in Table 3. The MIC for the positive control gentamicin was within the limit for *P. aeruginosa* ATCC27853 (0.5-2 µg/mL) and *E. coli* ATCC 25922 (0.25-1 µg/mL) indicating a correct procedure.

For all strains, the control substance CMS had lower MIC-values than the deca sulfomethylated polymyxins, except for the *A. baumannii* colistin sensitive strain where 3 out of 5 deca sulfomethylated polymyxins showed activity comparable to the CMS control. The MIC data show antimicrobial activity for all the deca sulfometylated polymyxins substances, but in general with lower activity compared to the CMS control.

TABLE 3

MIC (µg/mL) results for deca sulfomethylated polymyxins

| | Bacterial Strain | | | | |
|---|---|---|---|---|---|
| | E. coli | | P. aeruginosa | A. baumannii | K. pneumonia |
| Example | ATCC 25922 | DSA 443 | ATCC 27853 | ColistinS | #3010 |
| 1 (PE1-(SM)$_{10}^{1, 3, 5, 8, 9}$) | 8 | 16 | 8 | 4 | 16 |
| 2 (PE2-(SM)$_{10}^{1, 3, 5, 8, 9}$) | 8 | 16 | 8 | 4 | 16 |
| 3 (PE1-i-(SM)$_{10}^{1, 3, 5, 8, 9}$) | 8 | 16 | 8 | 4 | 16 |
| 4 (PE-(SM)$_{10}^{1, 3, 5, 8, 9}$) | 8 | 16 | 8 | 8 | 16 |
| 5 (PB-(SM)$_{10}^{1, 3, 5, 8, 9}$) | 16 | 16 | 8 | 8 | 16 |
| CMS | 2 | 4 | 4 | 4 | 4 |
| Gentamicin | 1 | >32 | 1 | >32 | 0.125 |

Example 7

Preparation of Tetra (Nγ-Bis-Sulfomethyl) DAB1,5,8,9 Polymyxin E1 (PE1-(SM)81,5,8,9 (FIG. 2))

Sodium bisulfite—formaldehyde adduct (9.80 g, 68.5 mmol) was dissolved in water (100 mL) and added 37% HCl (1.75 g, 17.7 mmol). Then polymyxin E1 (11.7 g, 10.0 mmol) was slowly added to the stirred solution. The resultant dispersion was then heated to 40° C. for 10 h and subsequently lyophilized to a white solid.

400 mg of the sulfomethylated polymycin E1 was dissolved in 20 mL 50% methanol and loaded a Waters Nova Pak C18, 6 µm, 60 Å, 40×310 mm mounted in a Waters Prep LC Universal Base at a flow of 20 mL/min. The column was equilibrated with A-eluent before application of substance solution.

The A-eluent was CH3CN: 10 mM Triethylamine 40 mM NaCl Buffer, 1:9

The B-eluent was CH3CN: 10 mM Triethylamine 40 mM NaCl Buffer, 4:6

The elution system was isocratic 0-5 min 100% A-eluent and during 20 min 100% A to 50% A as a linear gradient.

Figure 11:
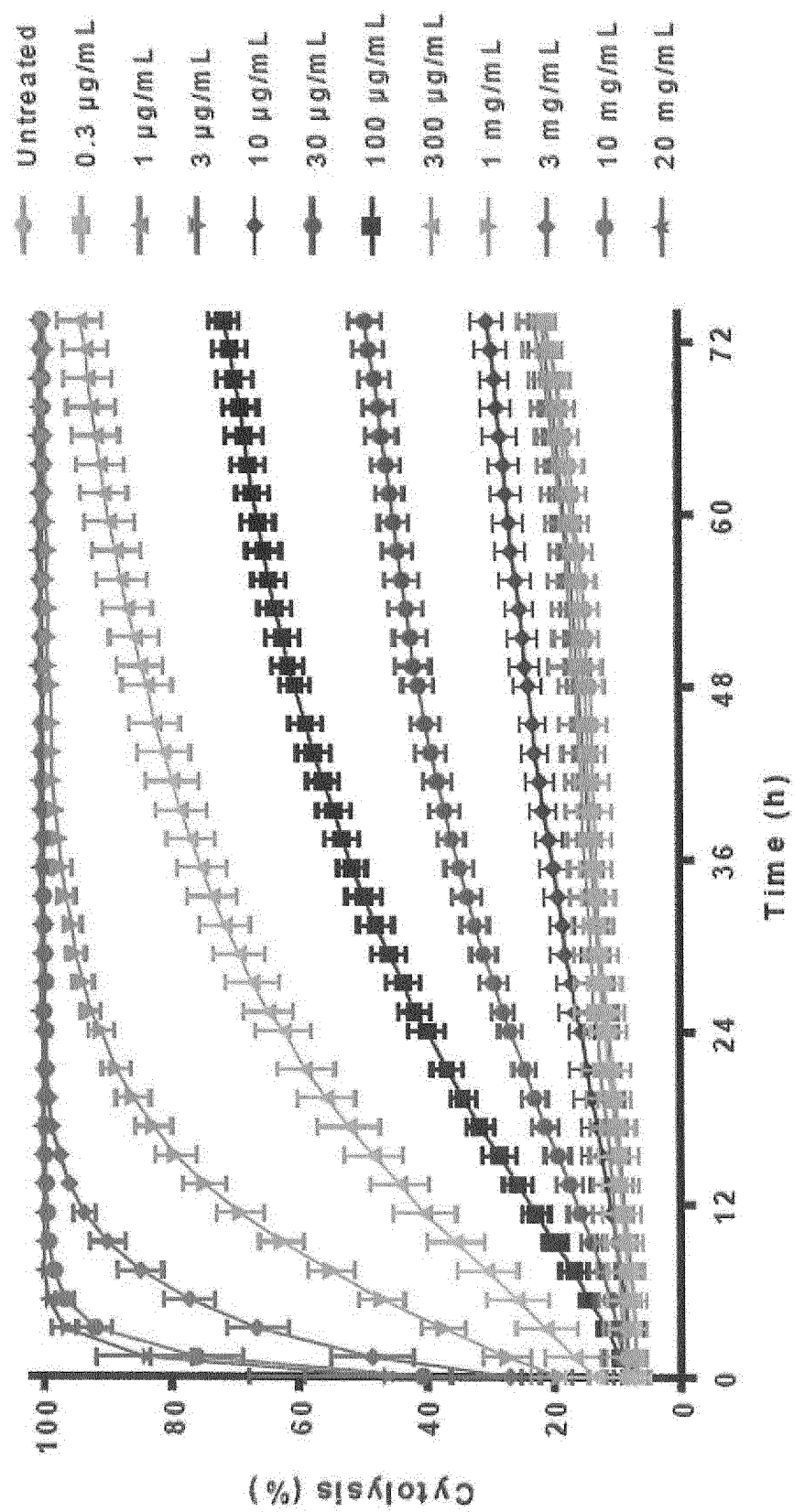
FIG. 11. Percent Cytolysis of HK-2 cells in the presence of Colistin (Sigma, C4461)
FIG. 12. Percent Cytolysis of HK-2 cells in the presence of penta ($N^\gamma$-bis-sulfomethyl) $DAB^{1,3,5,8,9}$ Polymyxin E1
Figure 12:
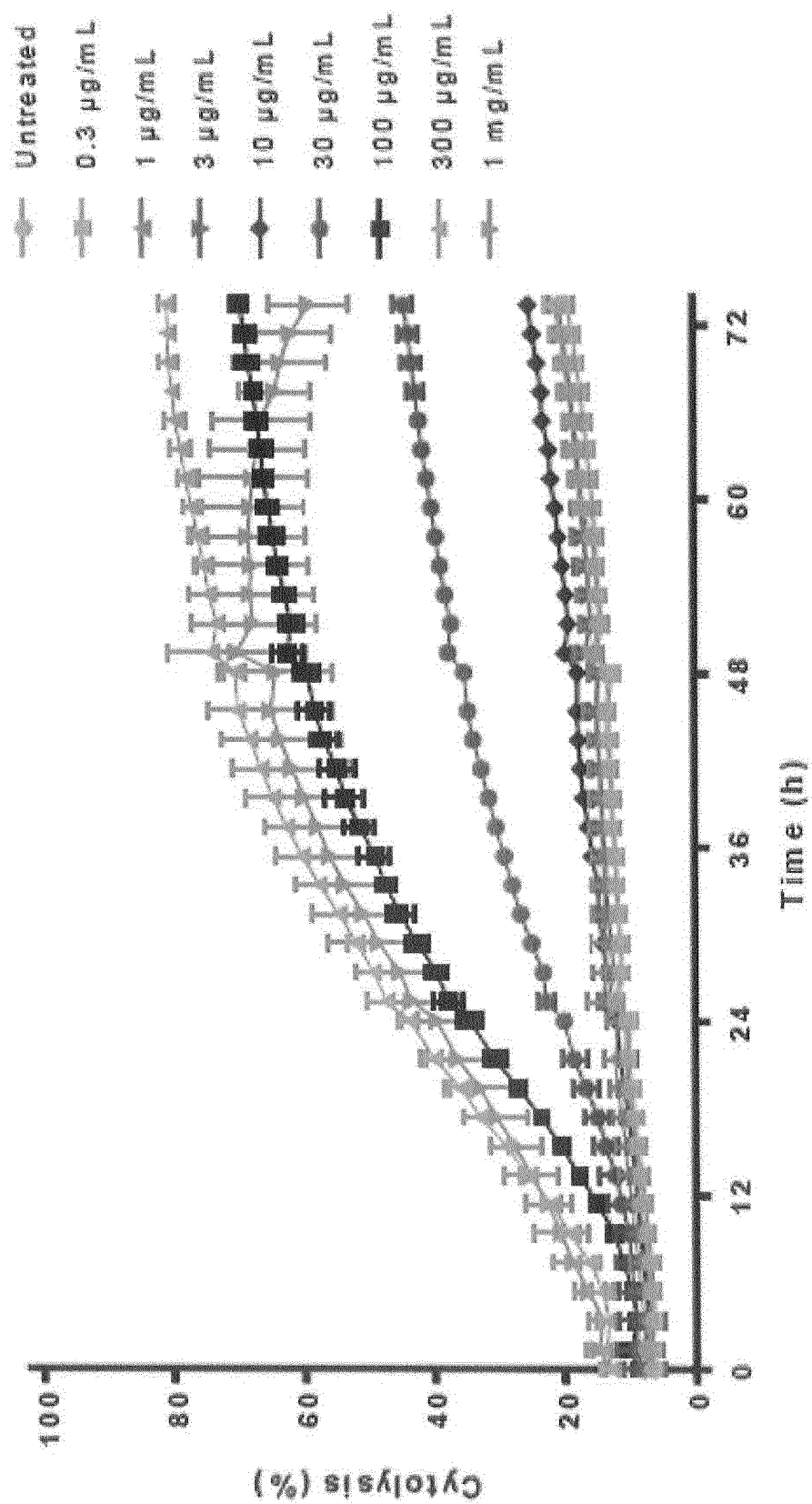
Figure 13:
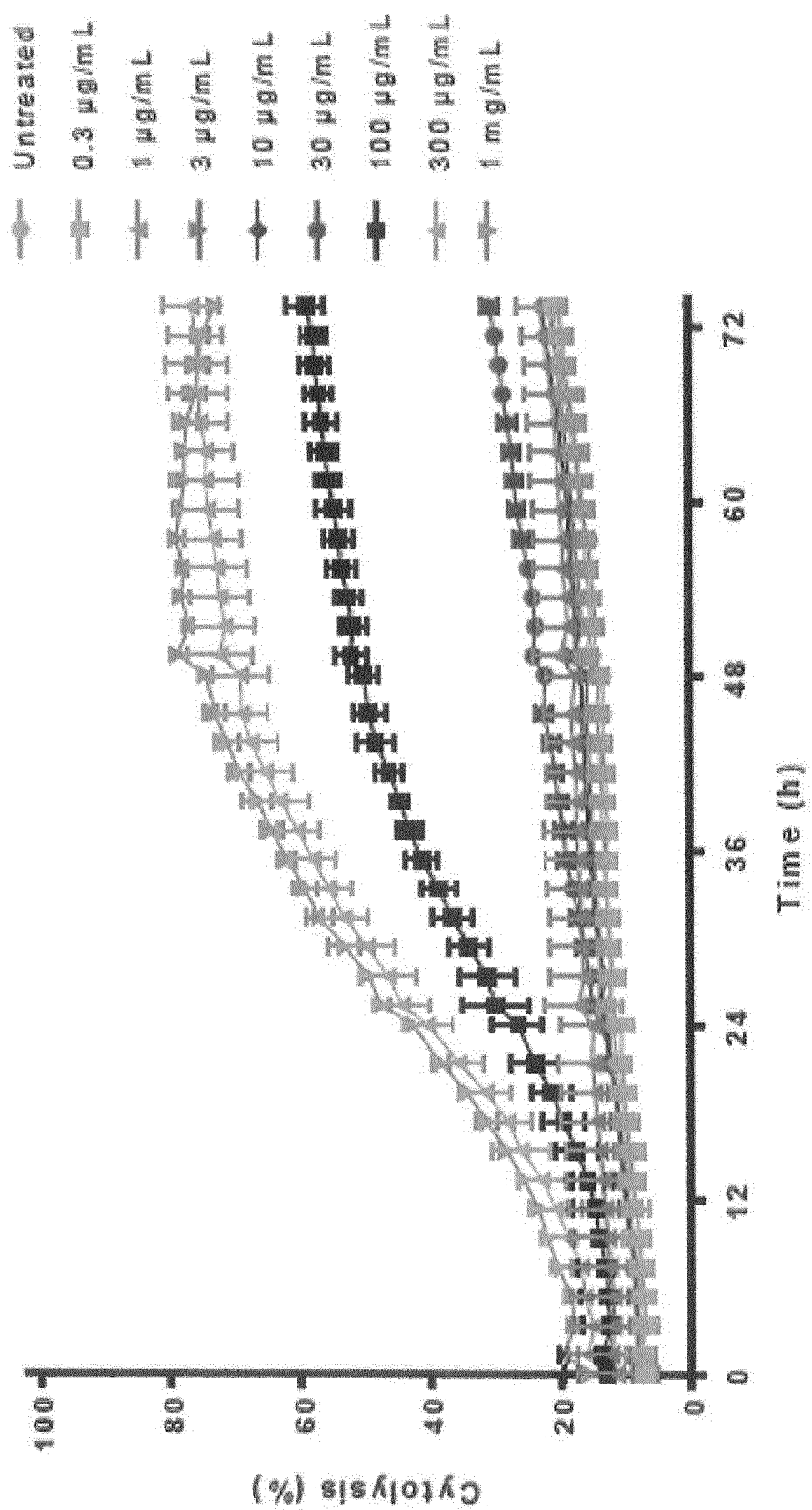
FIG. 13. Percent Cytolysis of HK-2 cells in the presence of penta (N$^\gamma$-bis-sulfomethyl) DAB$^{1,3,5,8,9}$ Polymyxin E2
Figure 14:
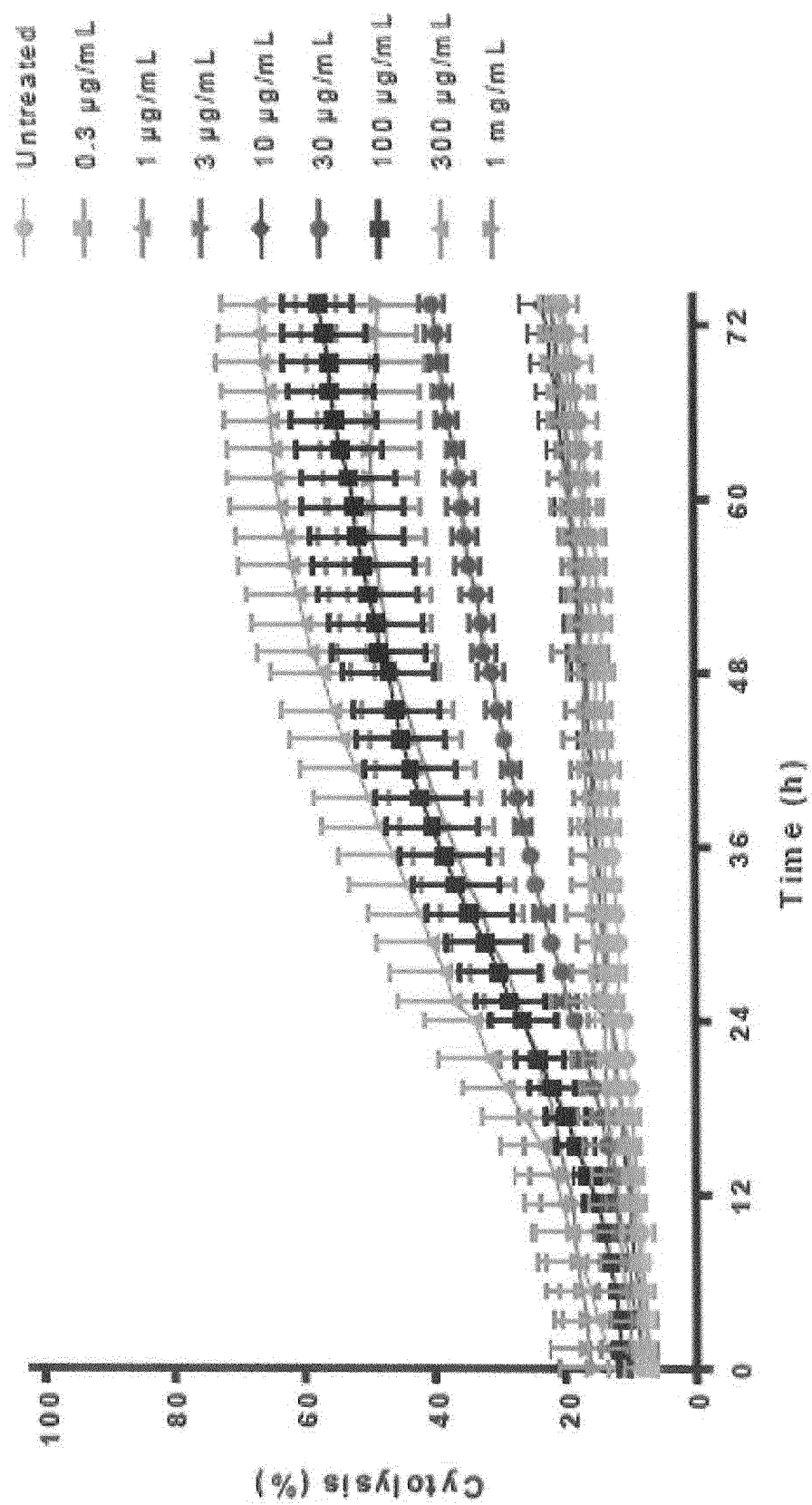
FIG. 14. Percent Cytolysis of HK-2 cells in the presence of penta (N$^\gamma$-bis-sulfomethyl)DAB$^{1,3,5,8,9}$ Polymyxin E1-i FIG. 15. Percent Cytolysis of HK-2 cells in the presence of penta (N$^\gamma$-bis-sulfomethyl)DAB$^{1,3,5,8,9}$ Polymyxin B
Figure 15:
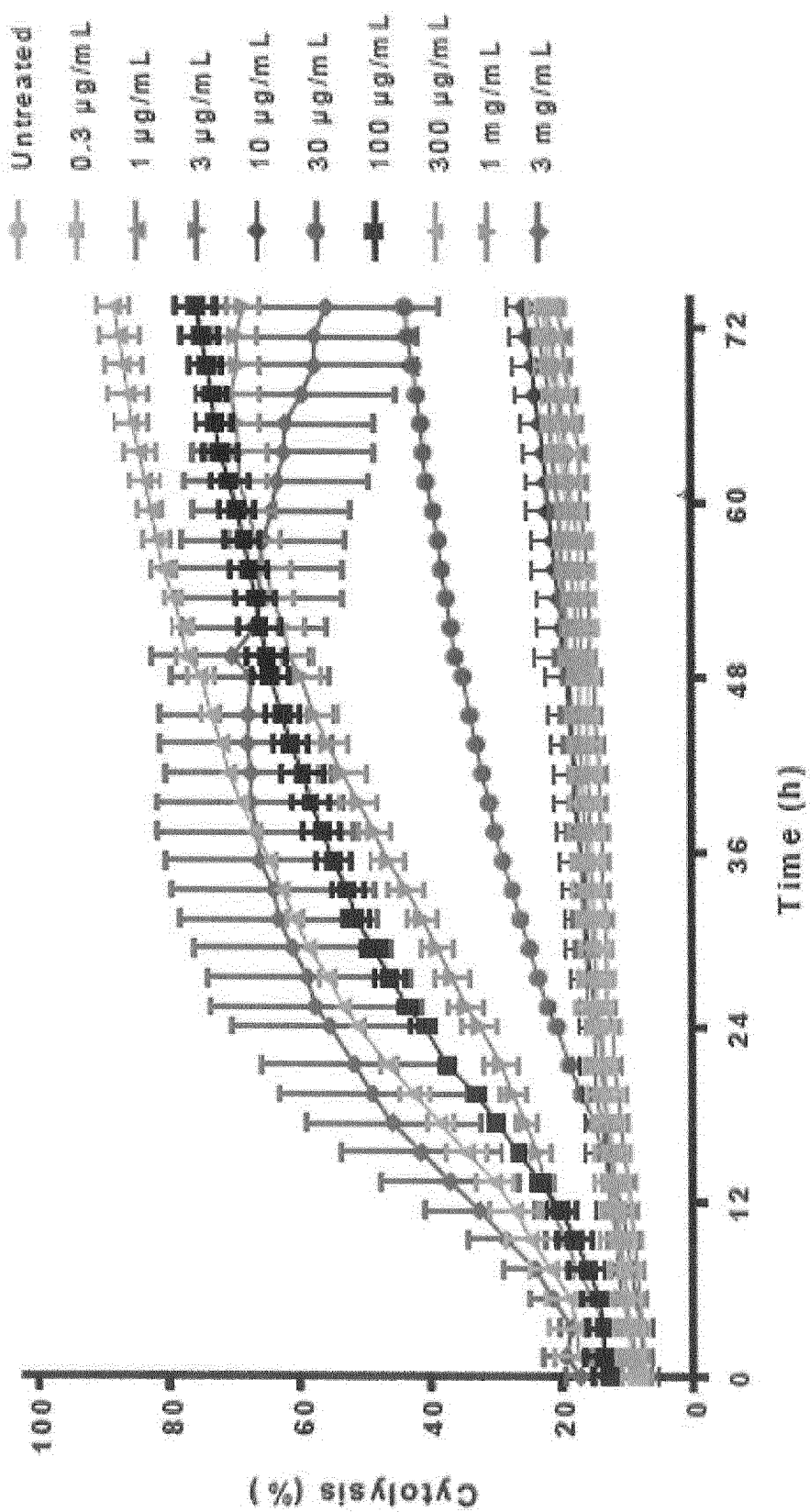

The first 5 major peaks were collected and analyzed. The first major peak at RT 12 min were PE1-(SM)81,5,8,9. The fractions were stored in freezer at −80° C. before further work up. The fast melted still cold 50-100 mL fractions with PE1-(SM)81,5,8,9 (FIG. 11) were diluted with 100% CH3CN to give ca. 4% water in CH3CN. The diluted fractions containing 15-30 mg PE1-(SM)8 with 75-85% purity, were vac-evaporated to dryness and re-dissolved in 100% methanol and collected in the −20° C. freezer to give 150-300 mg substance.

The substances were prep. HPLC reprocessed in the same manner as above and finally de-salted and polished as in Example 1. The product was determined by 1H-, 13C-, and 15N-NMR spectroscopy UHPLC with gradient on reverse phase (CSH C18, 1.7 μm, 150×2.1 mm) of the purified PE1-(SM)81,5,8,9 showed a single peak, with octa sulfomethylated polymyxins. The purity of the PE1-(SM)81,5,8,9 was 94% when the column eluent was monitored at 210 nm. Analysis was also performed through direct infusion of the octa and hexa sulfonated Colistin mixture using ESI-TOF MS (negative mode): calc. m/z for $C_{61}H_{108}N_{16}Na_{80}37S8$ [M]=2096.4 Found for the PE1-(SM)81,5,8,9 [M+8Na]-2 m/z 1025.2, and $[M+7Na]^3$ m/z 675.8.

TABLE 4

MIC (μg/ml) results for octa sulfomethylated polymyxin E1

| | Bacterial strain | | | |
|---|---|---|---|---|
| | E. coli ATCC 25922 | P. aeruginosa ATCC27853 | A. baumannii | K. pneumonia |
| (PE1-(SM)$_8$[1, 5, 8, 9] | 8 | 8 | 4 | 16 |

Example 8

Preparation of Tri (Nγ-Bis-Sulfomethyl) DAB1,5,9 Polymyxin E1 (Abbreviated: PE1-(SM)61,5,9 (FIG. 3))

Sodium bisulfite—formaldehyde adduct (9.80 g, 68.5 millimol) was dissolved in water (100 mL) and added 37% HCl (1.75 g, 17.7 mmol. Then polymyxin E1 (11.7 g, 10.0 mmol) was slowly added to the stirred solution. The resultant dispersion was then heated to 40° C. for 10 h and subsequently lyophilized to a white solid.

400 mg of the sulfomethylated polymyxin E1 was dissolved in 20 mL 50% methanol and loaded a Waters Nova Pak C18, 6 μm, 60 Å, 40×310 mm mounted in a Waters Prep LC Universal Base at a flow of 20 mL/min. The column was equilibrated with A-eluent before application of substance solution.

The A-eluent was CH3CN: 10 mM Triethylamine 40 mM NaC Buffer, 1:9

The B-eluent was CH3CN: 10 mM Triethylamine 40 mM NaCl Buffer, 4:6

The elution system was isocratic 0-5 min 100% A-eluent and during 20 min 100% A to 50% A as a linear gradient.

The first 5 major peaks were collected and analyzed. The last major peak at 22 min were PE1-(SM)61,5,9 (FIG. 3). The fractions were stored in a freezer at −80° C. before further work up. The fast melted still cold 50-100 mL fractions with PE1-(SM)61,5,9 were diluted with 100% CH3CN to give ca. 4% water in CH3CN. The diluted fractions containing 15-30 mg PE1-(SM)61,5,9 with 75-85% purity, were vac-evaporated to dryness and re-dissolved in 100% methanol and collected in the −20° C. freezer to give 150-300 mg substance.

The substances were prep. HPLC reprocessed in the same manner as above and finally de-salted and polished as in Example 1. The product was determined by NMR spectroscopy.

UHPLC with gradient on reverse phase (CSH C18, 1.7 μm, 150×2.1 mm) showed a single peak, with PE1-(SM)61, 5,9. The purity of the PE1-(SM)61,5,9 was 87% when the column eluent was monitored at 210 nm. Analysis was also performed through direct infusion of the octa and hexa sulfomethylated Polymyxin E1 using ESI-TOF MS (negative mode): calc. m/z for $C_{59}H_{106}N_{16}Na_{60}31S6$ [M]=1864.5 Found for PE1-(SM)61,5,9 [M+8 Na]-2 m/z 909.3 and [M+7Na]-3 m/z 598.5

TABLE 5

MIC (μg/mL) results for hexa sulfomethylated polymyxin E1

| | Bacterial strain | |
|---|---|---|
| | E. coli ATCC 25922 | P. aeruginosa ATCC27853 |
| PE1-(SM)$_6$[1, 5, 9] | 8 | 8 |

Example 9

In Vitro Toxicity Studies

HK-2 cells (human papillomavirus 16 transformed cell line from proximal tube of kidney nephron) were seeded in 96 well plates and cultured in Keratinoyctes serum free medium with 0.05 mg/mL Bovine Pituitary Extract and 5 ng/mL EGF for 24 hours. Cells were treated with the specified compounds in the presence of Sytox Green which penetrates damaged cell membranes only.

Time-lapse imaging was performed with 1 image every 2 hours showing the percentage of cytolysed cells. Results are visualized in FIGS. 11-15 and indicate a difference between colistin and the deca sulfomethylated Polymyxins regarding the ability to lyse HK-2 cells in vitro. The difference is apparent for any concentration above 100 μg/mL, and most prominent during the first 24 hours of the treatment.

Although a full and complete description is believed to be contained herein, certain patent and non-patent references may include certain essential subject matter. To the extent that these patent and non-patent references describe essential subject matter, these references are hereby incorporated by reference in their entirety. It is understood that the meanings of the incorporated subject matter are subservient to the meanings of the subject matter disclosed herein.

The invention claimed is:

1. A composition comprising at least one polymyxin or a salt thereof represented by formula (I)

(I)

[Chemical structure of formula (I) showing cyclic peptide with R1-R8 substituents]

wherein
R¹ is an aliphatic linear or branched $C_6$-$C_{10}$ acyl group, or

[Chemical structure: N-phenyl-2-oxopyridine-5-carbonyl group]

R⁵ is —CH(CH₃)₂, —CH₂CH(CH₃)₂, —CH(CH₃)CH₂CH₃, or —CH₂C₆H₅;
R⁶ is —CH(CH₃)₂, —CH₂CH(CH₃)₂, or —CH(CH₃)CH₂CH₃;
R², R³, R⁴, R⁷ and R⁸ are each —(CH₂)$_x$CH₂N(CH₂SO₃M)₂;
wherein x is 0 or 1; and
wherein M is a monovalent cation; and
wherein the at least one polymyxin or salt thereof is present in an amount of at least 50% by ultra-high performance liquid chromatography.

2. The composition of claim 1, wherein R¹ is heptanoyl, methylheptanoyl, octanoyl, methyloctanoyl, nonanoyl, methylnonanoyl or decyl.

3. The composition of claim 2, wherein R¹ is heptanoyl, (S)-6-methylheptanoyl, (S)-7-methylheptanoyl, octanoyl, (S)-6-methyloctanoyl, nonanoyl, (S)-6-methylnonanoyl, (S)-7-methylnonanoyl, (S)-8-methylnonanoyl, or decanoyl.

4. The composition of claim 1, wherein M is selected from the group consisting of Na⁺, K⁺, $H_mN(C_{1-4}alkyl)_n^+$, or combinations thereof, where m is 0-4 and n is 0-4 with the proviso that m+n=4.

5. The composition of claim 1, wherein the at least one polymyxin or salt thereof is present in an amount of at least 10% by UHPLC, at least 20% by UHPLC, at least 30% by UHPLC, at least 40% by UHPLC, at least 50% by UHPLC, at least 60% by UHPLC, at least 70% by UHPLC, at least 80% by UHPLC, at least 90% by UHPLC, at least 95% by UHPLC, at least 97% by UHPLC, at least 98% by UHPLC, or at least 99% by UHPLC.

6. The composition of claim 1, wherein x is 1 and M is H⁺, Na⁺ or K⁺.

7. The composition of claim 6, wherein each of R², R³, R⁴, R⁷ and R⁸ is —CH₂CH₂N(CH₂SO₃M)₂.

8. The composition of claim 6, wherein the at least one polymyxin or salt thereof is present in an amount of at least 10% by UHPLC, at least 20% by UHPLC, at least 30% by UHPLC, at least 40% by UHPLC, at least 50% by UHPLC, at least 60% by UHPLC, at least 70% by UHPLC, at least 80% by UHPLC, at least 90% by UHPLC, at least 95% by UHPLC, at least 97% by UHPLC, at least 98% by UHPLC, or at least 99% by UHPLC.

9. The composition of claim 1, wherein the at least one polymyxin or salt thereof represented by formula (I) is selected from any one of (A) to (H), wherein
(A) R¹ is 6-methyloctanoyl; each of R², R³, R⁴, R⁷, and R⁸ is —CH₂CH₂N(CH₂SO₃M)₂; and each of R⁵ and R⁶ is —CH₂CH(CH₃)₂;
(B) R¹ is

[Chemical structure: N-phenyl-2-oxopyridine-5-carbonyl group]

each of R², R⁴, R⁷, and R⁸ is —CH₂CH₂N(CH₂SO₃M)₂; R³ is —CH₂N(CH₂SO₃M)₂; R⁵ is —CH₂C₆H₅; and R⁶ is —CH₂CH(CH₃)₂;
(C) R¹ is 6-methylheptanoyl; each of R², R³, R⁴, R⁷, and R⁸ is —CH₂CH₂N(CH₂SO₃M)₂; and each of R⁵ and R⁶ is —CH₂CH(CH₃)₂;
(D) R¹ is 6-methyloctanoyl; each of R², R³, R⁴, R⁷, and R⁸ is —CH₂CH₂N(CH₂SO₃M)₂; R⁵ is —CH(CH₃)CH₂CH₃; and R⁶ is —CH₂CH(CH₃)₂;
(E) R¹ is octanoyl; each of R², R³, R⁴, R⁷, and R⁸ is —CH₂CH₂N(CH₂SO₃M)₂; and each of R⁵ and R⁶ is —CH₂CH(CH₃)₂;
(F) R¹ is 7-methyloctanoyl; each of R², R³, R⁴, R⁷, and R⁸ is —CH₂CH₂N(CH₂SO₃M)₂; and each of R⁵ and R⁶ is —CH₂CH(CH₃)₂;
(G) R¹ is 6-methyloctanoyl; each of R², R³, R⁴, R⁷, and R⁸ is —CH₂CH₂N(CH₂SO₃M)₂; R⁵ is —CH₂C₆H₅; and R⁶ is —CH₂CH(CH₃)₂; and
(H) R¹ is 6-methylheptanoyl; each of R², R³, R⁴, R⁷, and R⁸ is —CH₂CH₂N(CH₂SO₃M)₂; R⁵ is —CH₂C₆H₅; and R⁶ is —CH₂CH(CH₃)₂.

10. The composition of claim 1, wherein the at least one polymyxin or salt thereof represented by formula (I) is selected from any one of (A) to (H), wherein
(A) R¹ is 6-methyloctanoyl; each of R², R³, R⁴, R⁷, and R⁸ is —CH₂CH₂N(CH₂SO₃Na)₂; and each of R⁵ and R⁶ is —CH₂CH(CH₃)₂;
(B) R¹ is

[Chemical structure: N-phenyl-2-oxopyridine-5-carbonyl group]

each of R², R⁴, R⁷, and R⁸ is —CH₂CH₂N(CH₂SO₃Na)₂; R³ is —CH₂N(CH₂SO₃Na)₂; R⁵ is —CH₂C₆H₅; and R⁶ is —CH₂CH(CH₃)₂;
(C) R¹ is 6-methylheptanoyl; each of R², R³, R⁴, R⁷, and R⁸ is —CH₂CH₂N(CH₂SO₃Na)₂; and each of R⁵ and R⁶ is —CH₂CH(CH₃)₂;
(D) R¹ is 6-methyloctanoyl; each of R², R³, R⁴, R⁷, and R⁸ is —CH₂CH₂N(CH₂SO₃Na)₂; R⁵ is —CH(CH₃)CH₂CH₃; and R⁶ is —CH₂CH(CH₃)₂;

(E) $R^1$ is octanoyl; each of $R^2$, $R^3$, $R^4$, $R^7$, and $R^8$ is —$CH_2CH_2N(CH_2SO_3Na)_2$; and each of $R^5$ and $R^6$ is —$CH_2CH(CH_3)_2$;

(F) $R^1$ is 7-methyloctanoyl; each of $R^2$, $R^3$, $R^4$, $R^7$, and $R^8$ is —$CH_2CH_2N(CH_2SO_3Na)_2$; and each of $R^5$ and $R^6$ is —$CH_2CH(CH_3)_2$;

(G) $R^1$ is 6-methyloctanoyl; each of $R^2$, $R^3$, $R^4$, $R^7$, and $R^8$ is —$CH_2CH_2N(CH_2SO_3Na)_2$; $R^5$ is —$CH_2C_6H_5$; and $R^6$ is —$CH_2CH(CH_3)_2$; and (H) $R^1$ is 6-methylheptanoyl; each of $R^2$, $R^3$, $R^4$, $R^7$, and $R^8$ is —$CH_2CH_2N(CH_2SO_3Na)_2$; $R^5$ is —$CH_2C_6H_5$; and $R^6$ is —$CH_2CH(CH_3)_2$.

11. A pharmaceutical composition comprising a therapeutically effective amount of any one of the compositions of claim 1 and optionally a pharmaceutically acceptable excipient.

12. A method of treating a gram-negative bacterial infection in an infected patient, comprising administering to the patient the pharmaceutical composition of claim 11.

13. The method of claim 12, wherein the infection is caused by *Pseudomonas aeruginosa*, *Acinetobacter baumannii*, *Klebsiella pneumoniae*, *Escherichia coli*, *Enterobacter aerogenes*, or a combination thereof.

14. A method of manufacturing a polymyxin or a salt thereof represented by formula (I)

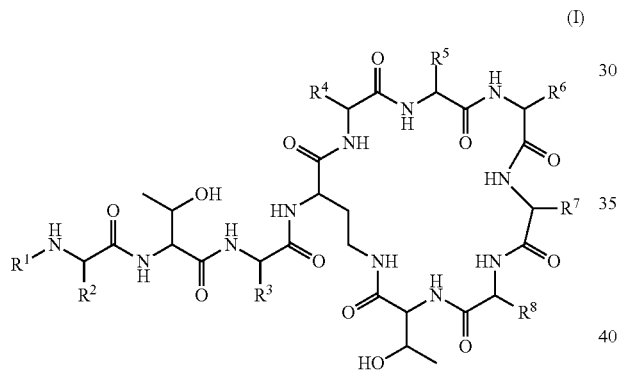

wherein
$R^1$ is an aliphatic linear or branched $C_6$-$C_{10}$ acyl group, or

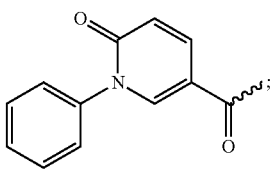

$R^5$ is —$CH(CH_3)_2$, —$CH_2CH(CH_3)_2$, —$CH(CH_3)CH_2CH_3$, or —$CH_2C_6H_5$;
$R^6$ is —$CH(CH_3)_2$, —$CH_2CH(CH_3)_2$, or —$CH(CH_3)CH_2CH_3$;
$R^2$, $R^3$, $R^4$, $R^7$ and $R^8$ is $(CH_2)_xCH_2N(CH_2SO_3M)_2$;
wherein x is 0 or 1; and
wherein M is a monovalent cation; and
wherein the at least one polymyxin or salt thereof is present in an amount of at least 50% by ultra-high performance liquid chromatography;
comprising:
a) providing a polymyxin or a salt thereof represented by formula (I)

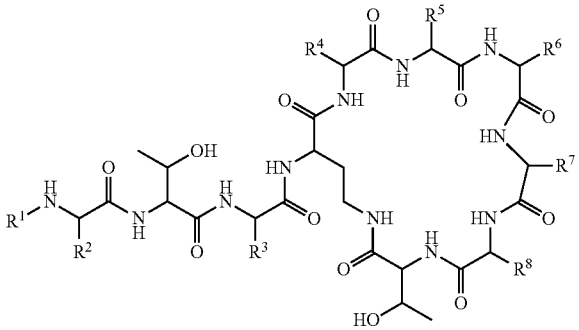

wherein
$R^1$ is an aliphatic linear or branched $C_6$-$C_{10}$ acyl group, or

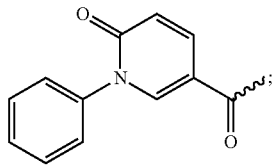

$R^5$ is —$CH(CH_3)_2$, —$CH_2CH(CH_3)_2$, —$CH(CH_3)CH_2CH_3$, or —$CH_2C_6H_5$;
$R^6$ is —$CH(CH_3)_2$, —$CH_2CH(CH_3)_2$, or —$CH(CH_3)CH_2CH_3$;
$R^2$, $R^3$, $R^4$, $R^7$ and $R^8$ is $(CH_2)_xCH_2NH_2$; and
wherein x is 0 or 1;

b) mixing the polymyxin of step a) with an excess of a methylsulfonation reagent; and c) heating the mixture obtained in step b) while keeping the pH of the mixture in the neutral range by addition of a base.

15. The method of claim 14, wherein the neutral pH is in the range of 7.0-7.5.

16. The method of claim 14, wherein the methylsulfonation reagent is a formaldehyde bisulfite adduct of formula

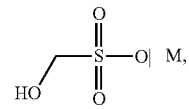

wherein M is a monovalent cation.

17. The method of 15, wherein the formaldehyde bisulfite adduct is in an aqueous solution.

18. The method of claim 15, wherein the monovalent cation is selected from the group consisting of sodium, potassium, lithium and ammonium.

19. The method of claim 14, further comprising d) cooling the mixture to ambient temperature and obtaining a crude product by precipitation.

20. The method of claim 14, wherein $R^6$ is —$CH_2CH(CH_3)_2$.

21. A polymyxin, or a salt thereof, obtained by the method of claim 14.

* * * * *